(12) United States Patent
Karanewsky et al.

(10) Patent No.: US 6,444,663 B2
(45) Date of Patent: Sep. 3, 2002

(54) TRICYCLIC COMPOUNDS FOR THE INHIBITION OF THE ICE/CED-3 PROTEASE FAMILY OF ENZYMES

(75) Inventors: Donald S. Karanewsky, Escondido; Steven D. Linton, San Diego, both of CA (US)

(73) Assignee: Idun Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/730,898

(22) Filed: Dec. 5, 2000

Related U.S. Application Data

(63) Continuation of application No. 09/338,874, filed on Jun. 23, 1999, now Pat. No. 6,187,771, which is a division of application No. 08/928,990, filed on Sep. 12, 1997, now Pat. No. 5,968,927, which is a continuation-in-part of application No. 08/710,621, filed on Sep. 20, 1996, now abandoned.

(51) Int. Cl.$^7$ .................................................. A61P 9/10
(52) U.S. Cl. .................................................. 514/212.05
(58) Field of Search .................................. 514/212.05

(56) References Cited

U.S. PATENT DOCUMENTS

| 5,504,080 A | 4/1996 | Karanewsky ............... 540/487 |
| 5,604,408 A | 2/1997 | Karanewsky et al. ....... 514/216 |
| 5,968,927 A | 10/1999 | Karanewsky et al. ....... 514/214 |
| 6,187,771 B1 | 2/2001 | Karanewsky et al. .. 514/212.05 |

FOREIGN PATENT DOCUMENTS

| EP | 0 519 748 A2 | 6/1992 |
| EP | 0 528 487 A2 | 8/1992 |
| EP | 0 533 226 A2 | 8/1992 |
| EP | 0 618 223 A2 | 3/1994 |
| EP | 0 623 592 A1 | 4/1994 |
| EP | 0 623 606 A2 | 4/1994 |
| WO | WO 91/15517 | 10/1991 |
| WO | WO 91/05071 | 3/1993 |
| WO | WO 93/09135 | 5/1993 |
| WO | WO 93/14777 | 8/1993 |
| WO | WO 94/03480 | 2/1994 |
| WO | WO 95/05192 | 2/1995 |

OTHER PUBLICATIONS

Baringa, M., "Cell Death Studies Yield Cancer Clues", *Science* 259:760–762 (1993).

De Lombaert et al., "Practical Synthesis of a Novel Tricyclic Dipeptide Mimetic Based on [6H]–Azepino Indoline Nucleus: Application to Angiotensin–Converting Enzyme Inhibition," *Tetrahedron Letters* 35:7513–7516.

Gagliardini et al., "Prevention of Vertebrate Neuronal Death by the crmA Gene," *Science* 263:826–828 (1994).

Howard et al., "IL–1–Converting Enzyme Requires Aspartic Acid Residues for Processing of the I1–1β Precursor at two Distinct Site and Does Not Cleave 31–kDa I1–1α," *J. Immunol.* 147:2964–2969 (1991).

Jones, "Amino Acid and Peptide Synthesis," Steven G. Davis ed., Oxford University Press, Oxford, pp. 25–41 (1992).

Lonnemann, et al., "Difference in the Synthesis and Kinetics of Release of Interleukin 1α, interleukin 1β and tumor necrosis factor from human mononuclear cells," *Eur. J. Immunol.* 19:1531–1536 (1989).

Miura, M. et al., "Induction of Apoptosis in Fibroblasts by IL–1β–Converting Enzyme, a Mammalian Homolog for the C. elegans Cell Death Gene ced–3," *Cell* 75:653–660 (1993).

Mosley, et al., "Determination of the minimum polypeptide lengths of the functionally active sites of human interleukins 1α and 1β," *Proc. Natl. Acad. Sci.* 84:4572–4576 (1987).

Nett–Fiordalisi, et al., "Macrophage Apoptosis in the Absence of Active Interleukin–1β–Converting Enzyme," *Journal of Leukocyte Biology* 58:717–724 (1995).

Nicholson et al., "Identification and Inhibition of the ICE/CED–3 Protease necessary for Mammalian Apoptosis," *Nature* 376:37–43 (1995).

Oppenheim, et al., "There is more than one Interleukin 1," *Immunology Today* 7:45–56 (1986).

Plattner, J.J. and D.W. Norbeck, in Drug Discovery Technologies, C.R. Clark and W.H. Moos, Eds. (Ellis Horwood, Chichester, England, 1990), pp. 92–126.

Robl et al., "Synthesis of Benzo–Fused 7,5–and 7,6–fused Azepinones as Conformationally Restricted Dipeptide Mometics," *Tetrahedron Letters* 36:1593–1596 (1995).

Sleath et al., "Substrate Specificity of the Protease That Processes Human Interleukin–1β," *J. Biol. Chem.* 265:14526–14528 (1992).

Thornberry et al., "A Novel Heterodimeric Cysteine Protease is Required for Interleukin–1β Processing in Monocytes," *Nature* 356:768:774 (1992).

Yuan et al., "The C. elegans Cell Death Gene ced–3 Encodes a Protein Similar to Mammalian Interleukin–1β–Converting Enzyme," *Cell* 75:641–652 (1993).

*Primary Examiner*—Bruce Kifle
(74) *Attorney, Agent, or Firm*—SEED Intellectual Property Law Group PLLC

(57) ABSTRACT

This invention is directed to novel tricyclic ICE/ced-3 family inhibitor compounds. The invention is also directed to pharmaceutical compositions of such tricyclic compounds, plus the use of such compositions in the treatment of patients suffering inflammatory, autoimmune and neurodegenerative diseases, and for the prevention of ischemic injury.

1 Claim, No Drawings

TRICYCLIC COMPOUNDS FOR THE INHIBITION OF THE ICE/CED-3 PROTEASE FAMILY OF ENZYMES

CROSS-REFERENCE TO RELATED APPLICATIONS

This application is a continuation of pending U.S. patent application No. 09/338,874, filed Jun. 23, 1999 now U.S. Pat. No. 6,187,771; which application is a divisional of U.S. patent application No. 08/928,990, filed Sep. 12, 1997, which issued on Oct. 19, 1999 as U.S. Pat. No. 5,968,927, which application is a continuation-in-part of U.S. patent application No. 08/710,621, filed Sep. 20, 1996, now abandoned.

BACKGROUND OF THE INVENTION

The present invention relates to novel classes of compounds which are inhibitors of interleukin-1β converting enzyme and related proteases ("ICE/ced-3 family of cysteine proteases"). This invention also relates to pharmaceutical compositions comprising these compounds and to methods of using such pharmaceutical compositions. The compounds, pharmaceutical compositions and methods of this invention are particularly well suited for inhibiting the protease activity of the ICE/ced-3 family and consequently, may be advantageously used as agents against interleukin-1 ("IL-1") mediated diseases, including inflammatory diseases, autoimmune diseases and neurodegenerative diseases and for inhibiting unwanted apoptosis in various disease states such as ischemic injury to the heart (e.g., myocardial infarction), brain (e.g., stroke), and kidney (e.g., ischemic kidney disease).

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today*, 7:45–56 (1986). As such, it is involved in the pathogenesis of chronic and acute inflammatory and autoimmune diseases. IL-1 is predominantly produced by peripheral blood monocytes as part of the inflammatory response. Mosely, B. S. et al., *Proc. Nat. Acad. Sci.*, 84:4572–4576 (1987); Lonnemann, G. et al., *Eur. J. Immunol.*, 19:1531–1536 (1989).

IL-1β is synthesized as a biologically inactive precursor, proIL-1β. ProIL-1β is cleaved by a cysteine protease called interleukin-1β converting enzyme ("ICE") between Asp-116 and Ala-117 to produce the biologically active C-terminal fragment found in human serum and synovial fluid. Sleath, P. R. et al., *J. Biol. Chem.*, 265:14526–14528 (1992); A. D. Howard et al., *J. Immunol.*, 147:2964–2969 (1991).

ICE is a cysteine protease localized primarily in monocytes. In addition to promoting the pro-inflammatory and immunoregulatory properties of IL-1β, ICE, and particulary its homologues, also appear to be involved in the regulation of cell death or apoptosis. Yuan, J. et al., *Cell*, 75:641–652 (1993); Miura, M. et al., *Cell*, 75:653–660 (1993); Nett-Giordalisi, M. A. et al. *J. Cell Biochem.*, 17B:117 (1993). In particular, ICE or ICE/ced-3 homologues are thought to be associated with the regulation of apoptosis in neurogenerative diseases, such as Alzheimer's and Parkinson's disease. Marx, J. and M. Baringa, *Science*, 259:760–762 (1993); Gagliardini, V. et al., *Science*, 263:826–828 (1994).

Thus, disease states in which inhibitors of the ICE/ced-3 family of cysteine proteases may be useful as therapeutic agents include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, ischemic diseases such as the myocardial infarction, stroke and ischemic kidney disease; immune-based diseases, such as hypersensitivity; auto-immune diseases, such as multiple sclerosis; bone diseases; and certain neurodegenerative diseases, such as Alzheimer's and Parkinson's disease.

ICE inhibitors represent a class of compounds useful for the control of the above-listed disease states. Peptide and peptidyl inhibitors of ICE have been described. However, such inhibitors have been typically characterized by undesirable pharmacologic properties, such as poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. These undesirable properties have hampered their development into effective drugs.

Accordingly, the need exists for compounds that can effectively inhibit the action of the ICE/ced-3 family of proteases, for use as agents for preventing unwanted apoptosis and for treating chronic and acute forms of IL-1 mediated diseases, such as inflammatory, autoimmune or neurodegenerative diseases.

The compounds of this invention incorporate a conformationally constrained dipeptide mimetic. This mimetic exhibits improved properties relative to their peptidic counterparts, for example, such as improved absorption and metabolic stability resulting in enhanced bioavailability.

SUMMARY OF THE INVENTION

One aspect of this invention is compounds of the formula:

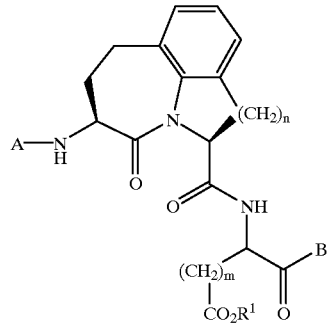

FORMULA 1 wherein:

n is 1 or 2;

m is 1 or 2;

A is $R^2CO-$, $R^3-O-CO-$, or $R^4SO_2-$;

a group of the formula:

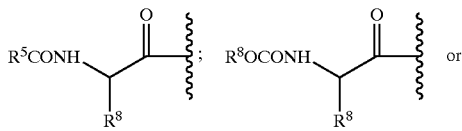

-continued $$R^7SO_2NH-\overset{\displaystyle O}{\underset{\displaystyle R^8}{C}}-$$

further wherein:

$R^1$ is a hydrogen atom, alkyl or phenylalkyl;

$R^2$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^3$ is alkyl, cycloalkyl, (cycloalkyl)alkyl, phenylalkyl or (substituted phenyl)alkyl;

$R^4$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^5$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^6$ is alkyl, cycloalkyl, (cycloalkyl)alkyl, phenylalkyl, or (substituted phenyl)alkyl;

$R^7$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^8$ is an amino acid side chain chosen from the group consisting of natural and unnatural amino acids;

B is a hydrogen atom, a deuterium atom, alkyl, cycloalkyl, (cycloalkyl)alkyl, phenyl, phenylalkyl, substituted phenyl, (substituted phenyl)alkyl, heteroaryl, (heteroaryl)alkyl, or a halomethyl group;

a group of the formula:

—CH$_2$XR$^9$;

wherein $R^9$ is phenyl, substituted phenyl, phenylalkyl, (substituted phenyl)alkyl, heteroaryl, or (heteroaryl)alkyl; and X is an oxygen or a sulfur atom;

a group of the formula:

—CH$_2$—O—CO-(aryl);

a group of the formula:

—CH$_2$—O—CO-(heteroaryl);

a group of the formula:

—CH$_2$—O—PO—(R$^{10}$)R$^{11}$;

wherein $R^{10}$ and $R^{11}$ are independently selected from a group consisting of alkyl, cycloalkyl, phenyl, substituted phenyl, phenylalkyl, and (substituted phenyl)alkyl;

or a pharmaceutically-acceptable salt thereof.

A further aspect of the instant invention are pharmaceutical compositions comprising a compound of the above Formula 1 and a pharmaceutically-acceptable carrier therefor.

Another aspect of this invention involves a method for treating an autoimmune disease comprising administering an effective amount of a pharmaceutical composition discussed above to a patient in need of such treatment.

Yet another aspect of the instant invention is a method of treating an inflammatory disease comprising administering an effective amount of a pharmaceutical composition discussed above to a patient in need of such treatment.

A further aspect of the instant invention is method of treating a neurodegenerative disease comprising administering a pharmaceutically effective amount of a pharmaceutical composition discussed above to a patient in need of such treatment.

Yet another aspect of the instant invention is a method of preventing ischemic injury to a patient suffering from a disease associated with ischemic injury comprising administering an effective amount of a pharmaceutical composition discussed above to a patient in need of such treatment.

DETAILED DESCRIPTION

One aspect of the instant invention is compounds of the Formula 1:

FORMULA 1

[Chemical structure of Formula 1]

wherein:

n is 1 or 2;

m is 1 or 2;

A is $R^2CO-$, $R^3-O-CO-$, or $R^4SO_2-$;

a group of the formula:

$$R^5CONH-\overset{\displaystyle O}{\underset{\displaystyle R^8}{C}}-\ ;\quad R^8OCONH-\overset{\displaystyle O}{\underset{\displaystyle R^8}{C}}-\ \text{or}$$

$$R^7SO_2NH-\overset{\displaystyle O}{\underset{\displaystyle R^8}{C}}-\ ;$$

further wherein:

$R^1$ is a hydrogen atom, alkyl or phenylalkyl;

$R^2$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^3$ is alkyl, cycloalkyl, (cycloalkyl)alkyl, phenylalkyl, or (substituted phenyl)alkyl;

$R^4$ is alkyl, cycloalkyl, (cycloalkyl)alkyl, phenyl, phenylalkyl, substituted phenyl, (substituted phenyl)alkyl, heteroaryl, or (heteroaryl) alkyl;

$R^5$ is alkyl, cycloalkyl, (cycloalkyl) alkyl, phenyl, phenylalkyl, substituted phenyl, (substituted phenyl)alkyl, heteroaryl, or (heteroaryl) alkyl;

$R^6$ is alkyl, cycloalkyl, (cycloalkyl)alkyl, phenylalkyl, or (substituted phenyl)alkyl;

$R^7$ is alkyl, cycloalkyl, (cycloalkyl)alkyl, phenyl, phenylalkyl, substituted phenyl, (substituted phenyl)alkyl, heteroaryl, or (heteroaryl)alkyl;

$R^8$ is an amino acid side chain chosen from the group consisting of natural and unnatural amino acids;

B is a hydrogen atom, a deuterium atom, alkyl, cycloalkyl, (cycloalkyl)alkyl, phenyl, phenylalkyl, (substituted)phenyl, (substituted)phenylalkyl, heteroaryl, (heteroaryl)alkyl, or halomethyl;

a group of the formula

—CH$_2$XR$^9$;

wherein R$^9$ is phenyl, phenylalkyl, substituted phenyl, (substituted phenyl)alkyl, heteroaryl, or (heteroaryl)alkyl; and X is an oxygen or a sulfur atom;

a group of the formula:

—CH$_2$—O—CO—(aryl);

a group of the formula:

—CH$_2$—O—CO—(heteroaryl);

a group of the formula:

—CH$_2$—O—PO—(R$^{10}$)R$^{11}$;

wherein R$^{10}$ and R$^{11}$ are independently selected from a group consisting of alkyl, cycloalkyl, phenyl, substituted phenyl, phenylalkyl, and (substituted phenyl)alkyl;

or a pharmaceutically-acceptable salt thereof.

As used in the above formula, the term "alkyl" means substituted or unsubstituted a straight chain or branched C$_1$ to C$_8$ carbon chain such as methyl, ethyl, tert-butyl, isopropyl, n-octyl, and the like. Suitable substituents include carboxy, protected carboxy, amino, protected amino, halo, hydroxy, protected hydroxy, nitro, cyano, monosubstituted amino, protected monosubstituted amino, disubstituted amino, C$_1$ to C$_1$ alboxy, C$_1$ to C$_7$ acyl, C$_1$ to C$_7$ acyloxy, and the like.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more, and preferably one or two, moieties chosen from the groups consisting of halogen, hydroxy, protected hydroxy, cyano, nitro, trifluoromethyl, C$_1$ to C$_7$ alkyl, C$_1$ to C$_7$ alkoxy, C$_1$ to C$_7$ acyl, C$_1$ to C$_7$ acyloxy, carboxy, protected carboxy, carboxymethyl, protected carboxymethyl, hydroxymethyl, protected hydroxymethyl, amino, protected amino, (monosubstituted) amino, protected (monosubstituted)amino, (disubstituted) amino, carboxamide, protected carboxamide, N-(C$_1$ to C$_6$ alkyl)carboxamide, protected N-(C$_1$ to C$_6$ alkyl) carboxamide, N,N-di(C$_1$ to C$_6$ alkyl)carboxamide, trifluoromethyl, N-((C$_1$ to C$_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy) phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

The terms "halo" and "halogen" refer to the fluoro, chloro, bromo or iodo groups. There can be one or more halogen, which are the same or different. Preferred halogens are chloro and fluoro.

The term "aryl" refers to aromatic five and six membered carbocyclic rings. Six membered rings are preferred.

The term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. These five-membered or six-membered rings are fully unsaturated.

Furthermore, the above optionally substituted five-membered or six-membered rings can optionally be fused to a aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined above substituted with the same groups as listed for a "substituted alkyl" group. The term "(monosubstituted)amino" refers to an amino group with one substituent chosen from the group consisting of phenyl, substituted phenyl, alkyl, substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different. The term "heteroaryl (alkyl)" denotes an alkyl group as defined above, substituted at any position by a heteroaryl group, as above defined.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); ammonium; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine, and acetic acid-like counter-ions such as acetate and trifluoroacetate. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and includes organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula 1 may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in Organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl groups and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group. The related term "protected hydroxy" denotes a hydroxy group bonded to one of the above hydroxy protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type blocking groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl) isopropoxycarbonyl, 1,1-diphenylethyl-1-oxycarbonyl, 1,1-diphenylpropyl-1-oxycarbonyl, 2-(3,5-dimethoxyphenyl) propyl-2-oxycarbonyl ("Ddz"), 2-(p-toluyl)propyl-2- oxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxy-carbonyl, α-2,4,5,-tetramethylbenzyloxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy)benzyloxycarbonyl and the like; the benzoylmethylsulfonyl group, 2,2,5,7,8-pentamethylchroman-6-sulfonyl group ("PMC") dithiasuccinoyl ("Dts"), the 2-(nitro) phenylsulfenyl group ("Nps"), the diphenyl-phosphine oxide group and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised ed., Springer-Verlag, New York, N.Y., 1984 and 1993, and J. M. Stewart and J. D. Young, "Solid Phase Peptide Synthesis," 2nd ed., Pierce Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The terms "natural and unnatural amino acids" (α-amino acid) refers to both the naturally occurring amino acids and other "non-protein" α-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of "non-protein" alpha-amino acids include hydroxylysine, citrulline, kynurenine, (4-aminophenyl)alanine, 3-(2'-naphthyl)alanine, 3-(1'-naphthyl)alanine, methionine sulfone, (t-butyl)alanine, (t-butyl)glycine, 4-hydroxyphenylglycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxykynurenine, 3-aminotyrosine, trifluoromethyl-alanine, 2-thienylalanine, (2-(4-pyridyl)ethyl)cysteine, 3,4-dimethoxy-phenylalanine, 3-(2'-thiazolyl)alanine, ibotenic acid, 1-amino-1-cyclopentane-carboxylic acid, 1-amino-1-cyclohexanecarboxylic acid, quisqualic acid, 3-(trifuoromethylphenyl)alanine, (cyclohexyl)glycine, thiohistidine, 3-methoxytyrosine, elastatinal, norleucine, norvaline, alloisoleucine, homoarginine, thioproline, dehydroproline, hydroxyproline, homoproline, α-amino-n-butyric acid, cyclohexylalanine, 2-amino-3-phenylbutyric acid, phenylalanine substituted at the ortho, meta, or para position of the phenyl moiety with one or two of the following: a ($C_1$ to $C_4$) alkyl, a ($C_1$ to $C_4$)alkoxy, halogen or nitro groups or substituted with a methylenedioxy group; β-2- and 3-thienylalanine, β-2- and 3-furanylalanine, β-2-, 3- and 4-pyridylalanine, β-(benzothienyl-2- and 3-yl) alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-(sulfo)tyrosine, 3-(carboxy)tyrosine, 3-(phospho)tyrosine, the 4-methane sulfonic acid ester of tyrosine, 4-methane phosphonic acid ester of tyrosine, 3,5-diiodotyrosine, 3-nitrotyrosine, ε-alkyl lysine, and delta-alkyl ornithine. Any of these α-amino acids may be substituted with a methyl group at the alpha position, a halogen at any aromatic residue on the α-amino side chain, or an appropriate protective group at the O, N, or S atoms of the side chain residues. Appropriate protective groups are discussed above.

Depending on the choice of solvent and other conditions known to the practitioner skilled in the art, compounds of this invention may also take the hemi-ketal, hemi-acetal, ketal or acetal form, which forms are included in the instant invention.

In addition, it should be understood that the equilibrium forms of the compounds of this invention may include tautomeric forms. All such forms of these compounds are expressly included in the present invention.

Also, it will be understood by those skilled in the art that when B in Formula 1 is a hydrogen atom, a semicarbazone may be formed with the resulting aldehyde. Such semicarbazones are also included as compounds of Formula 1, as well as the pharmaceutical compositions containing those compounds. Such semicarbazones include, for example, semicarbazone derivative of the optimal groups and embodiments of the 4-oxo butanoic acid derivatives of the oxoazepino indole and oxo-azepino quinoline compounds set forth below.

An optimal group of compounds of Formula 1 exists when in the above Formula n is 1, and more so when m is 1. These compounds will be referred to herein as the "oxoazepino indole" compounds.

An optimal group of oxoazepino indole compounds exists when B in Formula 1 is a hydrogen atom, compounds referred to herein as "4-oxobutanoic derivatives". One embodiment of note of such 4-oxobutanoic acid derivatives occurs when A in Formula 1 is a group of the formula $R^2CO—$, more so when $R^2$ is 2-(carboxy)eth-1-yl, 2-(phenyl)eth-1-yl, methyl, napth-1-yl or phenyl, and especially so when $R^1$ is a hydrogen atom. Another embodiment of 4-oxobutanoic acid derivatives exists when A is a group of the formula $R^5—CO—NH—CHR^8—CO—$, more so when $R^5$ is a methyl group and $R^8$ is a group of the formula $—CH_2COOH$, and especially so when $R^1$ is a hydrogen atom. Yet another embodiment of 4-oxobutanoic acid derivatives of note has A as a group of the formula $R^6—O—CO—NH—CHR^8—CO—$, further wherein $R^6$ is a benzyl group and $R^8$ is a group of the formula $—CH_2—COOH$, and especially so when $R^1$ is a hydrogen atom. Still another embodiment of the 4-oxobutanoic derivatives occurs when A is a group of the formula $R^3$—O—CO— wherein $R^3$ is benzyl, and especially so when $R^1$ is a hydrogen atom.

Another optimal group of oxoazepino indole compounds occurs when B in Formula 1 is a monofluoromethyl group and are thus referred to as "monofluoromethyl derivatives." A noteworthy embodiment of monofluoromethyl derivatives has A as a group of the formula $R^3$—O—CO—, more so when $R^3$ is a benzyl group, and especially so when $R^1$ is a hydrogen atom.

A further optimal group of oxoazepino indole compounds occurs when B in Formula 1 is a group of the formula —CH$_2$—O—PO($R^{10}$)$R^{11}$. This group of compounds is referred to herein as "phosphinyloxy derivatives". A group of noteworthy phosphinyloxy derivatives has $R^{10}$ and $R^{11}$ each as phenyl groups. An embodiment of such diphenyl phosphinyloxy compounds exists wherein A in Formula 1 is a group of the formula $R^3$—O—CO— wherein $R^3$ is benzyl, and especially so when $R^1$ is a hydrogen atom.

Another optimal group of compounds of Formula 1 exists when in the above Formula n is 2, and more so when m is 1. These compounds will be referred to herein as the "oxoazepino quinoline" compounds.

An exemplary group of oxoazepino quinoline compounds occurs when B in Formula 1 is a hydrogen atom, more so when A is a group of the formula $R^3$—O—CO— wherein $R^3$ is benzyl, and especially so when $R^1$ is a hydrogen atom.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of exertion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the A group or the modified aspartic or glutamic residues attached to the tricyclic nucleus of the compounds of this invention.

The compounds of Formula 1 of this invention may be synthesized using conventional techniques. Advantageously, these compounds are conveniently synthesized from readily available starting materials.

Thus, compounds of the instant invention can be synthesized in general by combining a tricyclic nucleus set forth below in Formula 2:

FORMULA 2 with the modified aspartic and glutamic acid residues of Formula 3a–d:

FORMULA 3a

FORMULA 3b

FORMULA 3c

FORMULA 3d in the presence of a standard peptide coupling agents such as dicyclohexylcarbodiimide (DCC)/1-hydroxybenzotriazole (HOBt), BOP reagent, pyBOP, TBTU, EEDQ, 1-ethyl(3,3'-dimethyl-1'-aminopropyl)carbodiimide (EDAC)/HOBt, and the like, as discussed in J. Jones, "Amino Acid and Peptide Synthesis," Steven G. Davis ed., Oxford University Press, Oxford, pp. 25–41 (1992), herein incorporated by reference. In the above formula, APG is an amino protecting group. The amino protecting group is then removed and the resulting amine is combined with the substituted acyl group of Formula 4:

$R^c$—CO—X                    FORMULA 4 or the sulfonyl group of Formula 5:

$R^4SO_2$—X.                   FORMULA 5

In the above formulas, $R^1$ is as defined above, and $R^c$ is $R^2$, $R^3$—O, $R^4$, or any of the side chains containing $R^8$ as defined for group A in Formula 1. Of course, such moieties would have any hydroxy, carboxy or amino groups in the protected form so as not to interfere with the coupling reaction (Formula 3a–d), the acylation reaction (Formula 4) or the sulfonation reaction (Formula 5). X in the above Formulas represents a facile leaving group for the acylation or sulfonation reactions.

In the case where the coupling reaction was carried out with the amino alcohol of Formula 3c, the alcohol moiety must be oxidized to the corresponding carbonyl compound prior to removal of the protecting groups. Preferred methods for the oxidation reaction include Swern oxidation (oxalyl chloride-dimethyl sulfoxide, methylene chloride at −78° C. followed by triethylmine; and Dess-Martin oxidation (Dess- Martin periodinane, t-butanol, and methylene chloride.) The protecting groups contained in substructures of the Formula 2 and 3a–d are removed by methods well known in the art.

The tricyclic nucleus of Formula 2 is synthesized by methods known in the art. For example, see D. S. Karanewsky, U.S. Pat. No. 5,504,080 issued Apr. 2, 1996; J. A. Robl et al., *Tetrahedron Letters*, 36:1593–1596 (1995); and S. De Lombaert et al., *Tetrahedron Letters*, 35:7513–7516 (1994), all of which are incorporated herein by reference.

The modified aspartic or glutamic acid for Formula 3a–d can be elaborated by methods well known in the art. See, for example, European Patent Application 519,748; PCT Patent Application No. PCT/EP92/02472; PCT Patent Application No. PCT/US91/06595; PCT Patent Application No. PCT/US391/02339; European Patent Application No. 623,592; World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472, World Patent Application No. WO 93/09135; PCT Patent Application No. PCT/US93/03589; and PCT Patent Application No. PCT/US93/00481, all of which are herein incorporated by reference.

The acyl group of Formula 4 and the corresponding $R^4SO_2$ groups are also synthesized by methods well known in the art. See, for example, U.S. Pat. No. 5,504,080, issued Apr. 2, 1996, herein incorporated by reference. While this group can be elaborated once bonded to the tricyclic nucleus, it is preferable that it be intact before being attached to the nucleus.

Once the side chains of Formula 3 and Formula 4 or Formula 5 are bonded to the tricyclic nucleus of Formula 2, one skilled in the art would usually remove any amino, hydroxy, or carboxy-protecting groups to enhance the activity of the synthesized molecule.

Pharmaceutical compositions of this invention comprise any of the compounds of Formula 1, and pharmaceutically acceptable salts thereof, with any pharmaceutically acceptable carrier, adjuvant or vehicle (hereinafter collectively referred to as "pharmaceutically-accetable carriers"). Pharmaceutically acceptable carriers, adjuvants and vehicles that may be used in the pharmaceutical compositions of this invention include, but are not limited to, ion exchange, alumina, aluminum stearate, lecithin, serum proteins, such as human serum albumin, buffer substances such as the various phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyarylates, waxes, polyethylene-polyoxypropylene-block polymers, polyethylene glycol and wool fat.

An optimal group of pharmaceutical compositions of Formula 1 exists when in the above Formula n is 1, and more so when m is 1. These compositions will be referred to herein as the "oxoazepino indole" compostions.

An optimal group of oxoazepino indole compositions exists when B in Formula 1 is a hydrogen atom, compositions referred to herein as "4-oxobutanoic derivatives". One embodiment of note of such 4-oxobutanoic acid derivatives occurs when A in Formula 1 is a group of the formula $R^2CO$—, more so when $R^2$ is 2-(carboxy)eth-1-yl, 2-(phenyl)eth-1-yl, methyl, napth-1-yl or phenyl, and especially so when $R^1$ is a hydrogen atom.

Another embodiment of 4-oxobutanoic acid derivatives exists when A is a group of the formula $R^5$—CO—NH—$CHR^8$—CO—, more so when $R^5$ is a methyl group and $R^8$ is a group of the formula —$CH_2COOH$, and especially so when $R^1$ is a hydrogen atom. Yet another embodiment of 4-oxobutanoic acid derivatives of note has A as a group of the formula $R^6$—O—CO—NH—$CHR^8$—CO—, further wherein $R^6$ is a benzyl group and $R^8$ is a group of the formula —$CH_2$—COOH, and especially so when $R^1$ is a hydrogen atom. Still another embodiment of the 4-oxobutanoic derivatives occurs when A is a group of the formula $R^3$—O—CO— wherein $R^3$ is benzyl, and especially so when $R^1$ is a hydrogen atom.

Another optimal group of oxoazepino indole compositions occurs when B in Formula 1 is a monofluoromethyl group and are thus referred to as "monofluoromethyl derivatives." A noteworthy embodiment of monofluoromethyl derivatives has A as a group of the formula $R^3$—O—CO—, more so when $R^3$ is a benzyl group, and especially so when $R^1$ is a hydrogen atom.

A further optimal group of oxoazepino indole compositions occurs when B in Formula 1 is a group of the formula —$CH_2$—O—$PO(R^{10})R^{11}$. This group of compositions is referred to herein as "phosphinyloxy derivatives". A group of noteworthy phosphinyloxy derivatives has $R^{10}$ and $R^{11}$ each as phenyl groups. An embodiment of such diphenyl phosphinyloxy compositions exists wherein A in Formula 1 is a group of the formula $R^3$—O—CO— wherein $R^3$ is benzyl, and especially so when $R^1$ is a hydrogen atom.

Another optimal group of pharmaceutical compositions of Formula 1 exists when in the above Formula n is 2, and more so when m is 1. These compositions will be referred to herein as the "oxoazepino quinoline" compositions.

An exemplary group of oxoazepino quinoline compositions occurs when B in Formula 1 is a hydrogen atom, more so when A is a group of the formula $R^3$—O—CO— wherein $R^3$ is benzyl, and especially so when $R^1$ is a hydrogen atom.

The pharmaceutical compositions of this invention may be administered orally, parenterally, by inhalation spray, topically, rectally, nasally, buccally, vaginally or via an implated reservoir. Oral and parenteral administration are preferred. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carrier which are commonly used include lactose and corn starch. Lubricating agents, such as magnesium stearate, are also typically added. For oral administration in capsule form useful diluents include lactose and dried corn starch. When aqueous suspension are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible to topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of this invention may be employed in a conventional manner for the treatment of diseases which are mediated by IL-1 in mammals. Such methods of treatment, their dosage levels and requirements may be selected by those of ordinary skill in the art form available methods and techniques. For example, a pharmaceutical composition of this invention may be administered to a patient suffering from an IL-1 mediated disease in a pharmaceutically acceptable manner and in an amount effective to lessen the severity of that disease.

In addition, the compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexons and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical compositions according to this invention may be comprised of a combination of a compound of Formula 1 and another therapeutic or prophylactic agent.

The disease states which may be treated or prevented by the instant pharmaceutical compositions include, but are not limited to, inflammatory diseases, autoimmune diseases and neurodegenerative diseases, and for inhibiting unwanted apoptosis involved in ischemic injury, such as ischemic injury to the heart (e.g., myocardial infarction), brain (e.g., stroke), and kidney (e.g., ischemic kidney disease). Methods of administering an effective amount of the above-described pharmaceutical compositions to mammals, also referred to herein as patients, in need of such treatment (that is, those suffering from inflammatory diseases, autoimmune diseases, and neurodegenerative diseases,) are additional aspects of the instant invention.

Yet another aspect of the instant invention is a method of preventing ischemic injury to a patient suffering from a disease associated with ischemic injury comprising administering an effective amount of a pharmaceutical composition discussed above to a patient in need of such treatment.

Also, each of the methods directed to methods for treating inflammatory diseases, autoimmune diseases, neurodegenerative disease, and preventing ischemic injury emcompass using any of the optimal groups and embodiments of pharmaceutical compositions set forth above.

Inflammatory disease which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. Target neurodegenerative diseases include, for example, amyotrophic lateral sclerosis, Alzheimer's disease, Parkinson's disease, and primary lateral sclerosis. The pharmaceutical compositions of this invention may also be used to promote wound healing. Target diseases associated with harmful, thus unwanted apoptosis, in other words, those associated with ischemic injury, includes myocardial infarction, stroke, and ischemic kidney disease. The pharmaceutical compositions of this invention may also be used to treat infectious diseases, especially those involved with viral infections.

The term "effective amount" refers to dosage levels of the order of from about 0.05 mg to about 140 mg per kilogram of body weight per day for use in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of the compounds of Formula 1 that may be combined with the carrier materials to produce a single dosage form will vary depending upon the host treated and the particular mode of administration. For example, a formulation intended for the oral administration of humans may contain from 0.5 mg to 5 gm of a compound of Formula 1 compounded with an appropriate and convenient amount of carrier material which may vary from about 5 to about 95 percent of the total composition. Dosage unit forms will generally contain between from about 1 mg to about 500 mg of an active compound of Formula 1.

It will be understood, however, that the specific "effective amount" for any particular patient will depend upon a variety of factors including the activity of the specific compound employed, the age, body weight, general health, sex, diet, time of administration, route of administration, rate of excretion, drug combination and the severity of the particular disease undergoing therapy.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to the ICE/ced-3 family of cysteine protease or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cystine protease inhibitors will be evident to those of ordinary skill in the art.

In order that this invention be more fully understood, the following examples are set forth. These examples are for the purpose of illustration only and are not to be construed as limiting the scope of the invention in any way.

In the following Examples, proton NMR spectra were obtained at 300 MHZ; chemical shifts are quoted downfield from internal tetramethylsilane.

PREPARATION 1

PREPARATION 1

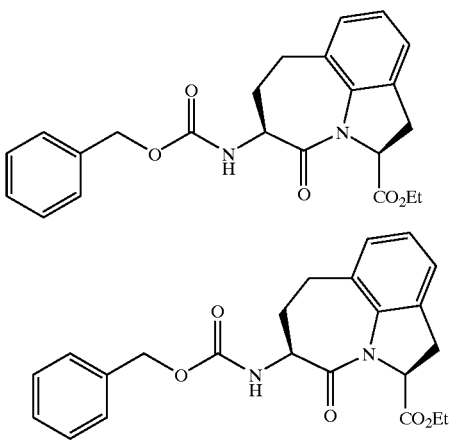

Preparation of (2S-cis)-5-Benzyloxycarbonylamino-1,2,4,5,6,7-Hexahydro-4-Oxoazepino[3,2,1-hi]indole-2-Carboxylic Acid, Ethyl Ester To a solution of (2S-cis)-5-amino-1,2,4,5,6,7-hexahydro-4-oxoazepino[3,2,1-hi]indole-2-carboxylic acid, ethyl ester (0.437 g, 1.73 mmol, prepared as described in Tetrahedron Letters 36, pp. 1593–1596 (1995) and U.S. Pat. No. 5,504,080 (Apr. 2, 1996)) in methylene chloride (4 mL) stirring at 0° C. was added benzyl chloroformate (0.370 mL, 2.6 mmol) and triethylamine (0.724 mL, 5.2 mmol) and the resulting mixture was stirred under nitrogen for 45 minutes. The reaction was quenched with water then partitioned between ethyl acetate and 5% aqueous potassium bisulfate solution. The aqueous layer was back-extracted two times with ethyl acetate, then the combined organic layers were washed with saturated sodium chloride solution, dried over sodium sulfate and evaporated to dryness. Purification of the crude product by flash chromatography on silica gel (S/P brand silica gel 60 Å, 230–400 mesh ASTM) eluting with ethyl acetate-hexane (2:1) gave 0.558 g (68%) of crude product. Trituration with ethyl acetate-hexane (1:4) gave 0.480 g of the title compound as white solid; m.p.: 139–140° C. TLC (ethyl acetate-hexane, 2:1): $R_f$=0.6; $^1$H-NMR (300 MHz, CDCl$_3$): δ 7.35–7.30 (m, 5H), 7.02–6.94 (m, 3H), 6.17 (d, J=5.4 Hz, 1H), 4.15 (q, J=7.1 Hz, 2H), 3.46 (dd, J=11.0, 16.7 Hz, 1H), 3.29 (m, 1H), 3.10 (d, J=116.5, 2H), 2.35 (m, 1H), 2.16 (m, 1H), 1.23 (t, J=7.2 Hz, 3H).

PREPARATION 2

PREPARATION 2

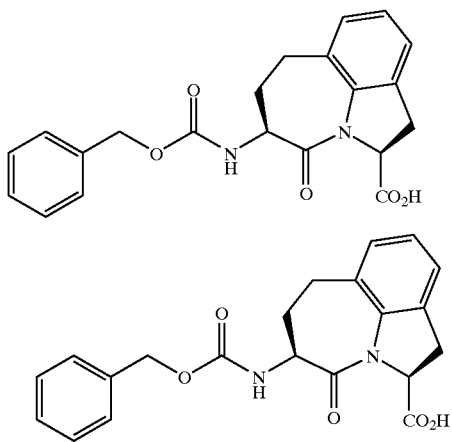

Preparation of (2S-cis)-5-Benzyloxycarbonylamino-1,2,4,5,6,7-Hexahydro-4-Oxoazepino[3,2,1-hi]indole-2-Carboxylic Acid To a solution of (2c-cis)-5-benzyloxycarbonylamino-1,2,4,5,6,7-hexahydro-4-oxoazepino[3,2,1-hi]indole-2-carboxylic acid, ethyl ester, (0.428 g, 1.05 mmol) in 1,4-dioxane (7.5 mL) and water (2.5 mL) was added 1M aqueous lithium hydroxide (1.6 mL, 1.6 mmol) and the resulting mixture was stirred at room temperature under nitrogen for 30 minutes. The reaction mixture was acidified to pH 3 with a 5% aqueous potassium bisulfate sodium chloride solution. The aqueous layer was back-extracted two times with ethyl acetate, and the combined organic layers were dried over sodium sulfate and evaporated to dryness to yield 0.395 g (99%) of title compound as a fine white solid; m.p.: 188–189° C. TLC (methylene chloride-methanol-acetic acid, 9:1:1): $R_f$=0.55; $^1$H-NMR (300 MHz, CDCl$_3$) δ 7.34–7.26 (m, 5H), 7.07–6.97 (m, 3H), 6.08 (d, J=5.7 Hz, 1H), 5.25 (dd, J=3.2, 9.8 Hz, 1H), 5.10 (s, 2H), 4.30 (m, 1H), 3.36 (m, 1H), 3.26 (m, 2H), 3.06 (d, J=12.0 Hz, 1H), 2.36 (m, 1H), 2.09 (m, 1H).

PREPARATION 3

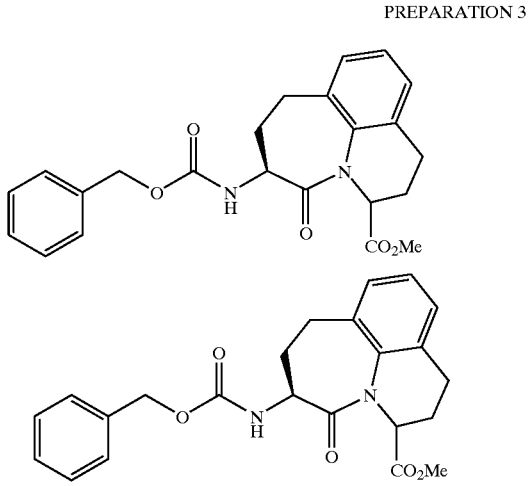

Preparation of (3R,S-cis)-6-Benzyloxycarbonylamino-5-oxo-2,3,4,5,6,7,8-hexahydro-1H-azepino[3,2,1-hi]quinoline-3-carboxylic acid, methyl ester To a solution of (3R,S-cis)-6-Amino-5-oxo-2,3,4,5,6,7,8-hexahydro-1H-azepino[3,2,1-hi]quinoline-3-carboxylic acid, methyl ester (0.570 g, 2.1 mmol, prepared as described in Tetrahderon Letters 36, pp. 1593–1596 (1995) and U.S. Pat. No. 5,504,080 (Apr. 2, 1996)) in methylene chloride (6 mL) stirring at 0° C. was added benzyl chloroformate (0.6 mL, 4.2 mmol) and triethylamine (1.2 mL, 8.4 mmol) and the resulting mixture was stirred under nitrogen for 30 minutes. The reaction was quenched with water then partitioned between ethyl acetate and 5% aqueous potassium bisulfate solution. The aqueous layer was back extracted two times with ethyl acetate, then the combined organic layers were washed with saturated sodium chloride solution, dried (sodium sulfate) and evaporated to dryness. Purification of the crude product by flash chromatography on silica gel (S/P brand silica gel 60 Å, 230-400 mesh ASTM) eluting with ethyl acetate-hexane (2:1) gave 0.643 g (76%) of of the title compound as a white foam. TLC (methylene chloride-methanol, 95:5) $R_f$=0.8. $^1$H-NMR (300 MHz, CDCl$_3$) δ 7.36–7.25 (m, 5H), 7.13–7.02 (m, 3H), 5.67 (d, J=7.8 Hz, 1H), 5.02 (t, J=9.15, 18.3 Hz, 2H), 4.34 (m, 1H), 3.70 (s, 3H), 3.16 (m, 1H), 2.69–2.56 (m, 5H), 2.06 (m, 1H). Mass spectrum: m/z 408 (M+H).

PREPARATION 4

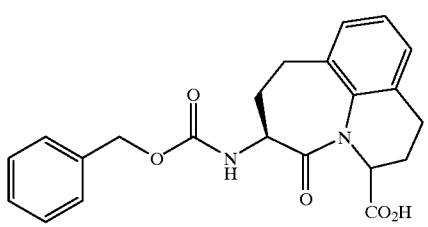

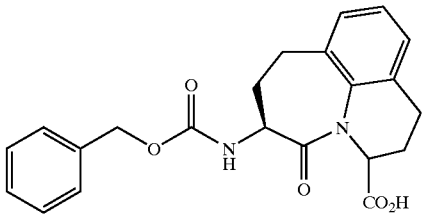

Preparation of (3R, S-cis)-6-Benzyloxycarbonylamino-5-oxo-2,3,4,5,6,7,8-hexahydro-1H-azepino [3,2,1-hi]quinoline-3-carboxylic acid To a solution of (3R,S-cis)-6-Benzyloxycarbonylamino-5-oxo-2,3,4,5,6,7,8-hexahydro-1H-azepino[3,2,1-hi]quinoline-3-carboxylic acid, methyl ester (0.622 g, 1.53 mmol) in 1,4-dioxane (10.5 mL) and water (3.5 mL) was added 1M aqueous lithium hydroxide (2.3 mL, 2.3 mmol) and the resulting mixture was stirred at room temperature under nitrogen for 1 hour. The reaction mixture was acidified to ca. pH 2 with a 5% aqueous potassium bisulfate solution, then partitioned between ethyl acetate and saturated sodium chloride solution. The aqueous layer was back extracted two times with ethyl acetate, and the combined organic layers were dried (sodium sulfate) and evaporated to yield 0.670 g of the title compound. TLC (methylene chloride-methanol-acetic acid, 32:1:1) $R_f$=0.35. $^1$H-NMR (300 MHz, CDCl$_3$) δ 7.38–7.28 (m, 5H), 7.13–7.04 (m, 3H), 5.72 (d, J=8.1 Hz, 1H), 5.03 (s, 2H), 4.35 (m, 1H), 3.77–3.67 (m, 5H), 3.10 (m, 1H), 2.72–2.52 (m, 5H), 2.07 (m, 1H), 1.70 (m, 1H).

PREPARATION 5

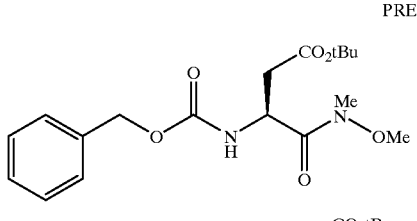

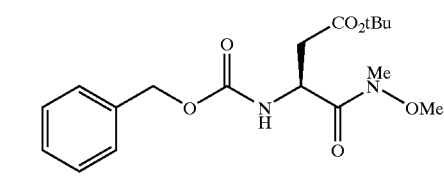

Preparation of N-(Benzyloxycarbonyl)-L-(N'-Methyl-N'-Methoxy)aspartamide β-(tert-Butyl Ester)

To a solution of N-(benzyloxycarbonyl)-L-aspartic acid-β-(tert-butyl)ester (14.65 g, 45.3 mmol, Bachem) in CH$_2$Cl$_2$ (150 mL) at 0° C. (ice bath) under a nitrogen atmosphere was added 1-hydroxybenzotriazole hydrate (7.29 g, 47.6 mmol, Aldrich) followed by 1-ethyl-3-(3',3'-dimethyl-1'-aminopropyl)carbodiimide hydrochloride (9.55 g, 49.8 mmol, Sigma). After stirring at 0° C. for 15 min., N,O-dimethylhydroxylamine hydrochloride (5.10 g, 52.3 mmol, Aldrich) and N-methylmorpholine (5.8 mL, 53 mmol, Aldrich) were added. The mixture was allowed to warm to room temperature over 3 hours then stirred at room temperature for 16 hours. The solution was concentrated under vacuum and the residue partitioned between ethyl acetate-5% KHSO$_4$ (200 mL each). The organic phase was washed in turn with 5% KHSO$_4$, saturated sodium bicarbonate and saturated sodium chloride solutions; dried over anhydrous sodium sulfate and evaporated to an oil. The oil was crystallized from hexane to give the title product (16.10 g, 97% yield) as a fluffy white crystalline solid. TLC (ethyl acetate), single spot (UV and PMA): $R_f$=0.37.

A similar procedure to the one above, starting with 29.3 g of N-(benzyloxycarbonyl)-L-aspartic acid-β-(tert-butyl) ester (2-fold scale up) gave 31.18 g (94% yield) of the title product.

PREPARATION 6

PREPARATION 6

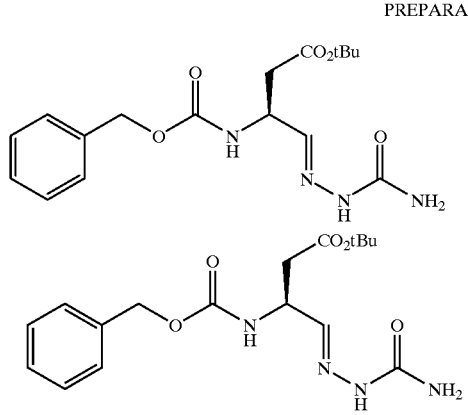

Preparation of N-(Benzyloxycarbonyl)-L-Aspartic Acid Semicarbazone β-(tert-Butyl)Ester To a solution of N-(benzyloxycarbonyl)-L-(N'-methyl-N'-methoxy)aspartamide β-(tert-butyl ester) (15.50 g, 42.3 mmol) in anhydrous ether (400 mL) at 0° C. (ice bath) under a nitrogen atmosphere was added dropwise to a 1.0 M solution of LiAlH$_4$ in ether (22.0 mL, 22.0 mmol, Aldrich) at such a rate as to keep the reaction solution temperature between 0–5° C. (addition time 15–20 min). After the addition of the lithium aluminum hydride reagent was complete, the mixture was stirred at 0–5° C. for 1 hr, then quenched by the dropwise addition of 0.3 N KHSO$_4$ solution (100 mL). The resultant mixture was transferred to a separatory funnel adding sufficient 5% KHSO$_4$ solution (75 mL) to dissolve the solids. The organic phase was separated and the combined aqueous washes back-extracted with ether (100 mL). The combined ether extracts were washed with saturated NaCl solution, dried over anhydrous sodium sulfate and concentrated in vacuo with minimal heating. TLC (ethyl acetate): streaky spot (UV and PMA) $R_f$=0.48. TLC (methanol/methylene chloride, 1:9) major spot (UV and PMA): $R_f$=0.75.

The crude aldehyde was immediately taken up in aqueous ethanol (45 mL water/105 mL alcohol), placed in an ice bath and treated with sodium acetate (3.82 g, 46.6 mmol) and semicarbazide hydrochloride (5.20 g, 46.6 mmol, Aldrich). The mixture was stirred at 0° C. (ice bath) under a nitrogen atmosphere for 3 hrs, allowed to warm to room temperature, and stirred overnight (16 hrs). Most of the ethanol was removed under vacuum and the residue partitioned between ethyl acetate and water (100 mL each). The organic phase was washed sequentially with 5% KHSO$_4$, saturated sodium bicarbonate and saturated sodium chloride solutions; dried over anhydrous sodium sulfate and evaporated to dryness. The crude product of this reaction was combined with that of two similar procedures starting with 15.40 g and 4.625 g of N-(benzyloxycarbonyl)-L-(N'-methyl-N'-methoxy) aspartamide β-(tert-butyl ester) (total: 35.525 g, 97 mmol) and these combined products were purified by flash chromotography on silica gel eluting with acetone/methylene chloride (3:7) then methanol-acetone-methylene chloride (0.5:3:7) to give pure title product (27.73 g, 78.5%) as a colorless foam. TLC (MeOH—CH$_2$Cl$_2$, 1:9): single spot (UV and PMA), $R_f$=0.51.

PREPARATION 7

PREPARATION 7

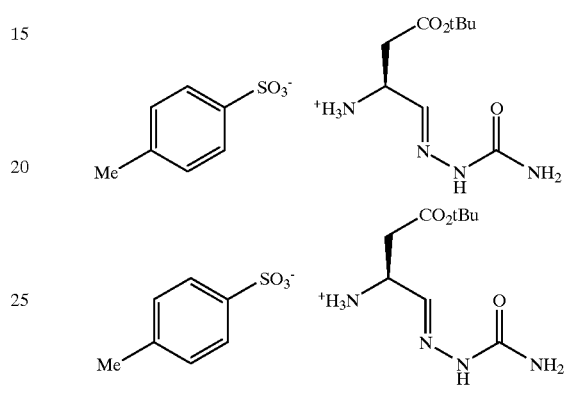

Preparation of L-Aspartic Acid Semicarbazone β-(tert-Butyl) Ester, p-Toluenesulfonate Salt To a solution of N-(benzyloxycarbonyl)-L-aspartic acid semicarbazone β-(tert-butyl)ester (13.84 g, 38.0 mmol) in absolute ethanol (250 mL) was added 10% Pd/C (1.50 g, Aldrich) and the resulting mixture stirred under an atmosphere of hydrogen (balloon) until TLC (methanol/methylene chloride, 1:9) indicated complete consumption of the starting material (60 min). Note: It is important to follow this reaction closely since the product can be over-reduced. The mixture was filtered though Celite and evaporated to an oil. The oil was chased with methylene chloride (2×75 mL) then with methylene chloride/toluene (1:1, 75 mL) to give the crude amine as a white crystalline solid. TLC (EtOAc-pyridine-AcOH-H$_2$O; 60:20:5:10) single spot (UV and PMA) $R_f$=0.24. Note: In this TLC system, any over-reduced product will show up immediately below the desired product, $R_f$=0.18 (PMA only).

The crude amine was taken up in CH$_3$CN (60 mL) and treated with a solution of p-toluenesulfonic acid monohydrate (7.22 g, 38.0 mmol) in acetonitrile (60 mL). The crystalline precipitate was collected, washed with acetonitrile and ether, and air-dried to give the title compound (13.95 g, 92% yield) as a white, crystalline solid.

The optical purity of this material was checked by conversion to the corresponding Mosher amide [1.05 equiv (R)-(−)-α-methoxy-α-(trifluoromethyl)phenylacetyl chloride, 2.1 equivalents of i-Pr$_2$NEt in CH$_2$Cl$_2$, room temperature, 30 min]. The desired product has a doublet at 7.13 ppm (1H, d, J=2.4 Hz, CH=N) while the corresponding signal for its diastereomer is at 7.07 ppm. The optical purity of the title compound obtained from the above procedure is typically >95:5.

PREPARATION 8

Assay for Inhibition of ICE/ced-3 Protease Family Activity

A. Determination of $IC_{50}$ Values

Fluorescence enzyme assays detecting the activity of the compounds of Formula 1 utilizing the recombinant ICE and CPP32 enzymes were performed essentially according to Thornberry et al. (*Nature*, 356:768:774 (1992)) and Nicholson et al. (*Nature*, 376:37-43 (1995)) respectively, (herein incorporated by reference) in 96 well microtiter plates. The substrate is Acetyl-Tyr-Val-Ala-Asp-amino-4-methylcoumarin (AMC) for the ICE assay and Acetyl-Asp-Glu-Val-Asp-amino-4-methylcoumarin for the CPP32, Mch2, Mch3 and Mch5 assays. Enzyme reactions were run in ICE buffer (25 mM HEPES, 1 mM EDTA, 0.1% CHAPS, 10% sucrose, pH 7.5) containing 2 mM DTT at room temperature in duplicate. The assays were performed by mixing the following components:

50 μL ICE, Mch2, Mch5, CPP32 (18.8, 38, 8.1 and 0.153 nM concentrations, respectively) or Mch3 (1 unit) enzyme in ICE buffer containing either 8.0 (ICE, Mch2, Mch3, CPP32) or 20 (Mch5) mM DTT;

50 μL compound of Formula 1 or ICE buffer (control); and

100 μL of 20 μM substrate.

The enzyme and the compound of Formula 1 to be assayed were allowed to preincubate in the microtitre plate wells for 30 minutes at room temperature prior to the addition of substrate to initiate the reaction. Fluorescent AMC product formation was monitored for one hour at room temperature by measuring the fluorescence emission at 460 nm using an excitation wavelength of 360 nm. The fluorescence change in duplicate (control) wells were averaged and the mean values were plotted as a function of inhibitor concentration to determine the inhibitor concentration producing 50% inhibition ($IC_{50}$). The results of this assay are set forth below in Table 1.

The reference compound for this assay was Cbz-ValAlaAsp-H and the values are denoted in Table 1 as "Reference".

TABLE 1

| Example No. | mICE $IC_{50}$ (μM) | CPP32 $IC_{50}$ (μM) | MCH-2 $IC_{50}$ (μM) | MCH-3 $IC_{50}$ (μM) | MCH-5 $IC_{50}$ (μM) |
|---|---|---|---|---|---|
| 3 | 0.019 | 1.03 | 40.1 | 6.96 | >10 |
| 7 | 0.694 | 0.0014 | 6.47 | 0.145 | 2.09 |
| 10 | 0.571 | 0.245 | 1.81 | 2.83 | 7.98 |
| 13 | 0.096 | 0.00052 | ND | 0.084 | 1.19 |
| 16 | 0.045 | 0.780 | >10 | 32.6 | 18.7 |
| 19 | 3.07 | 3.87 | >10 | >50 | >50 |
| 25 | 0.159 | 8.77 | >50 | >50 | 4.63 |
| 22 | 0.010 | 2.91 | >50 | 12.3 | 1.09 |
| 28 | 0.026 | 0.437 | 32.0 | 1.11 | 2.06 |
| Ref. | 0.064 | 47.0 | >10 | >10 | 2.96 |

B. Determination of the dissociation constant Ki and irreversible rate constant $k_3$ for irreversible inhibitors For the irreversible inhibition of a ICE/ced-3 Family Protease enzyme with a competitive irreversible inhibitor; using the model represented by the following formulas:

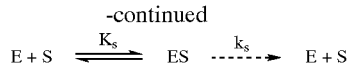

The product formation at time t may be expressed as:

$$[P]_t = [E]^T \left(\frac{[S]K_i}{[I]K_s}\right)\left(\frac{k_s}{k_3}\right)\left[1 - e^{-k_3 t/\left(1+\frac{K_i}{[I]}\left(1+\frac{[S]}{K_s}\right)\right)}\right] \quad \text{Equation 1}$$

where E, I, EI and E-I denote the active enzyme, inhibitor, non-covalent enzyme-inhibitor complex and covalent enzyme-inhibitor adduct, respectively. The $K_i$ value is the overall dissociation constant of the reversible binding steps, and $k_3$ is the irreversible rate constant. The [S] and $K_s$ values are the substate concentration and dissociation constant of the substrate bound to the enzyme, respectively. $[E]^T$ is the total enzyme concentration.

The above equations were used to determine the $K_i$ and $k_3$ values of a given inhibitor bound to a ICE/ced-3 family protease. Thus, a continuous assay was run for sixty minutes at various concentrations of the inhibitor and the substrate. The assay was formulated essentially the same as described above for generating the data in Table 1, except that the reaction was initiated by adding the enzyme to the substrate-inhibitor mixture. The $K_i$ and $k_3$ values were obtained by simulating the product AMC formation as a function of time according to Equation I. The results of this second assay are set forth below in Table 2.

The reference compound for this assay was Cbz-ValAlaAsp-$CH_2F$ and the values are denoted in Table 2 as "Reference".

TABLE 2

| | Example 31 | | Reference | |
|---|---|---|---|---|
| Enzyme | Ki (μM) | $k_3$/Ki (μM) | Ki (μM) | $k_3$/Ki ($M^{-1}s^{-1}$) |
| mICE | 0.0005 | 12,000,000 | 0.015 | 214,000 |
| CPP32 | 0.012 | 960,000 | 0.820 | 12,200 |
| MCH-2 | 0.033 | 25,000 | 0.594 | 2,950 |
| MCH-5 | 0.022 | 98,000 | 0.018 | 83,300 |

EXAMPLE 1

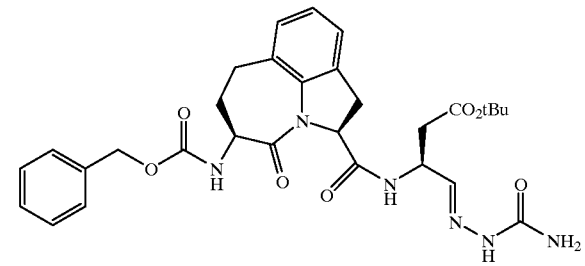

(2S-cis)-[5-Benzyloxycarbonylamino-1,2,4,5,6,7-Hexahydro-4-Oxoazepino[3,2,1-hi]indole-2-Carbonyl) amino]-4-Oxo-butanoic Acid tert-Butyl Ester Semicarbazone To a solution of (2S-cis)-5-benzyloxycarbonylamino-1,2,4,5,6,7-hexahydro-4-oxoazepino[3,2,1-hi]indole-2-carboxylic acid (0.375 g, 0.989 mol) in methylene chloride (7 mL) stirring at 0° C. under nitrogen was added 1-hydroxybenzotriazole hydrate (0.182 g, 1.19 mmol) and 1-ethyl-3-(3',3'-dimethy-1'-aminopropyl)carbodiimide hydrochloride (0.284 g, 1.48 mmol). After 15 minutes L-aspartic acid semicarbazone β-(tert-butyl) ester, p-toluenesulfonate salt (0.386 g, 0.989 mmol) and N-methylmorpholine (0.163 mL, 1.48 mmol) were added and the resultant reaction mixture allowed to come to room temperature within 1 hour. After stirring overnight, the reaction mixture was diluted with ethyl acetate and washed successively with 5% potassium bisulfate and saturated sodium chloride solutions; dried over sodium sulfate and evaporated to dryness. Purification of the crude product by flash chromatography on silica gel (S/P brand silica gel 60 Å, 230-400 mesh ASTM) eluting with 2% methanol-methylene chloride gave 0.463 g (79%) of the title compound as a white foam. TLC (methylene chloride-methanol, 9:1): $R_f$=0.5. $^1$H-NMR (300 MHz, CDCl$_3$): δ_8.42 (s, 1H), 7.82 (d, J=8.1 Hz, 1H), 7.32 (m, 5H), 7.07 (m, 3H), 5.94 (d, J=6.3 Hz, 1H), 5.26 (d, J=9 Hz, 1H), 5.10 (s, 2H), 4.82 (m, 1H), 4.35 (m, 1H), 3.56 (d, J=18 Hz, 1H), 3.27 (m, 2H), 3.07 (m, 1H), 2.64 (dd, J=4.7, 15.8 Hz, 1H), 2.44 (dd, J=6.6, 15.9 Hz, 2H), 2.22 (m, 1H), 1.30 (s, 9H). Mass spectrum: m/z 593 (M+H).

EXAMPLE 2

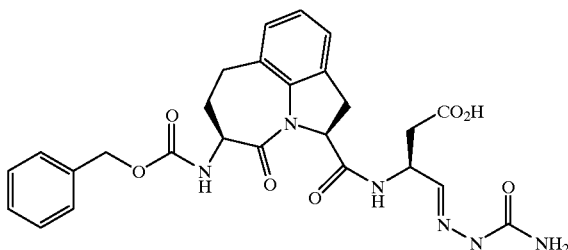

(2-cis)-[5-Benzyloxycarbonylarnno-1,2,4,5,6,7-hexadydro-4-oxoazepino[3,2,1-hi]indole-2-carbonyl)-amino]-4-oxo-butanoic acid semicarbazone To a solution of (2S-cis)-[5-benzyloxycarbonylamino-1,2,4,5,6,7-bexahydro-4-oxoazepino[3,2,1-hi]indole-2-carbonyl)amino]-4-oxo-butanoic acid tert-butyl ester semicarbazone (0.214 g, 0.362 mmol) in methylene chloride (1.5 mL) was added anisole (0.5 mL, 4.34 mmol) followed by trifluoroacetic acid (0.75 mL). After stirring at room temperature under nitrogen for 2 hours the reaction mixture was diluted with methylene chloride and evaporated, then chased twice with methylene chloride to give the title compound (0.195 g). TLC (methylene chloride-methanol, 95:5), $R_f$=0.2. $^1$H NMR (300 MHz, CDCl$_3$) δ_9.77 (bs, 1H), 8.32 (d, J=12 Hz, 1H), 8.12 (d, J-7.8 Hz, 1H), 7.31-7.27 (m, 5H) 7.13-7.04 (m, 3H), 6.64 (m, 1H) 5.32 (d, J=9.9 Hz, 1H), 5.12 (s, 2H), 4.86 (m, 1H), 4.41 (m, 1H), 3.56 (d, J=15 Hz, 1H), 3.25 (m, 2H), 3.10 (m, 2H), 2.64 (m, 2H), 2.28 (m, 2H).

EXAMPLE 3

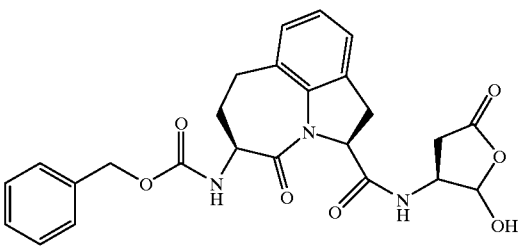

(2S-cis)-5-[Benzyloxycarbonylamino-1,2,4,5,6,7-hexahydro-4-oxoazepino[3,2,1-hi]indole-2-carbonyl)-amino]-4-oxo-butanoic acid (2-cis)-[5-Benzyloxycarbonylamino-1,2,4,5,6,7-hexadydro-4-oxoazepino [3,2,1-hi]indole-2-carbonyl)-amino]-4-oxo-butanoic acid semicarbazone (0.195 g, 0.36 mmol) was treated with a 3:1:1 solution of methanol-acetic acid-37% formaldehyde (2 mL) and the resulting mixture stirred under nitrogen for 1.5 hours. The reaction mixture was diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.073 g, (42%) of the title compound as a white solid after lyophilization; m.p. 101–104° C. TLC (methylene chloride-methanol-acetic acid, 97:2.5:0.5) $R_f$=0.45. $^1$H-NMR (300 MHz, CDCl$_3$) δ_7.45 (m, 1H), 7.30 (s, 5H), 7.07 (d, J=3.3 Hz, 1H), 7.00 (d, J=4.8 Hz, 2H), 6.12 (m, 1H), 5.17 (d, J=9.6 Hz, 1H), 5.07 (s, 2H), 4.49 (m, 1H), 4.28 (m, 1H), 3.46 (d, J=9.9 Hz, 1H), 3.30–3.12 (m, 2H), 3.04–2.99 (m, 1H), 2.83–2.76 (m, 1H), 2.46–2.33 (m, 2H), 2.03 (bs, 1H). Mass spectrum: m/z 480 (M+H).

EXAMPLE 4

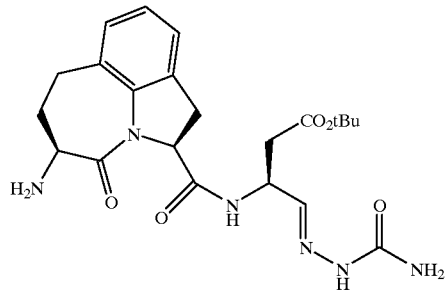

(2S-cis)-[5-Amino-1,2,3,4,5,6,7-hexahydro-4-oxoazepino[3,2,1-hi]indole-2-carbonyl)-amino]-4-oxo-butanoic acid tert-butyl ester semicarbazone 10% Palladium on carbon (0.180 g) was added to a solution of (2S-cis)-[5-benzyloxycarbonylamino-1,2,3,4,5,6,7-hexahydro-4-oxoazepino[3,2,1-hi]indole-2-carbonyl)-amino]-4-oxo-butanoic acid tert-butyl ester semicarbazone (0.308 g, 0.520 mmol) in methanol (27 mL) and the resulting mixture was hydrogenated using a balloon of hydrogen (1 atm, R.T.) for 18 hours. The mixture was filtered through Celite, evaporated to dryness, then chased two times with toluene to give the title compound as an off-white solid (0.215 g). TLC (methylene chloride-methanol, 9:1) $R_f$=0.15.

$^1$H-NMR (300 MHz, CDCl$_3$) δ 8.53 (s, 1H), 7.89 (d, J=7.6 Hz, 1H), 7.13 (m, 3H), 5.21 (dd, J=2.3, 10.14 Hz, 1H), 4.82 (m, 1H), 3.52 (m, 1H), 3.24 (dd, J=10.3, 16.3 Hz, 1H), 3.03 (m, 2H), 2.62 & 2.42 (AB, dd, J=4.2, 7.1, 15.7 Hz, 2H), 2.19 (m, 1H), 1.32 (s, 9H).

EXAMPLE 5

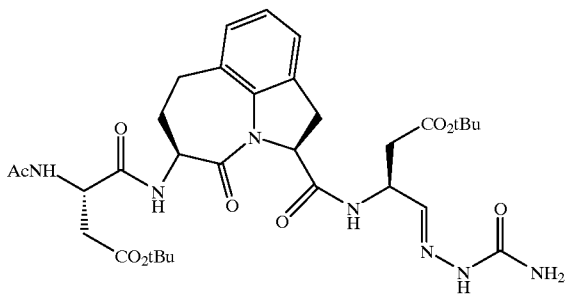

(2S-cis)-[5-(N-Acetyl-(S)-aspartyl-β-tert-butyl ester)amino-1,2,3,4,5,6,7-hexahydro-4-oxoazepino[3,2,1-hi]indole-2-carbonyl)-amino]-4-oxo-butanoic acid tert-butyl aster semicarbazone To a solution of N-acetyl aspartic acid, β-tert-butyl ester (0.120 g, 0.517 mmol) in methylene chloride (1.5 mL) stirring at 0° C. under nitrogen was added 1-hydroxybenzotriazole hydrate (0.086 g, 0.564 mmol) and 1-(3-dimethylaminopropyl)-3-ethylcarbodiimide hydrochloride (0.135 g, 0.705 mmol). After 15 minutes, a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.213 g, 0.47 mmol) in methylene chloride (2 mL) was added and the reaction was allowed to come to room temperature over 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 5% then 10% methanol-methylene chloride gave 0.126 g (41%) of the title compound as a white solid. TLC (methylene chloride-methanol, 9:1) R$_f$=0.4. $^1$H-NMR (300 MHz, CDCl$_3$) δ 9.63 (s, 1H), 8.32 (d, J=7.8 Hz, 1H), 7.82 (d, J=.6.6 Hz, 1H), 7.53 (d, J=4.8 Hz, 1H), 7.09 (m, 1H), 7.00 (m, 2H), 5.18 (d, J=8.1 Hz, 1H), 4.86 (m, 1H), 4.39 (m, 1H), 3.01 (m, 1H), 2.92 (dd, J=4.2, 14.7 Hz, 1H) 2.68 (d, J=12.3 Hz, 1H), 2.52 (m, 2H), 2.51 (m, 2H), 2.03 (s,3H), 1.39 (s, 9H), 1.24 (s, 9H).

EXAMPLE 6

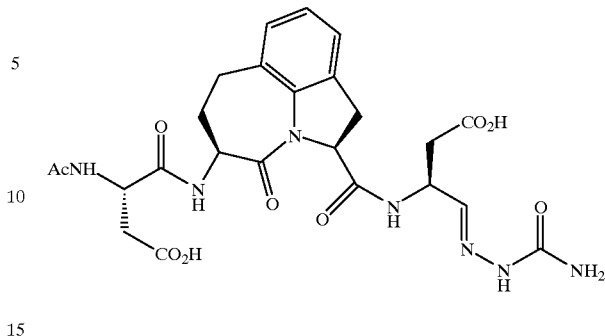

(2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic acid semicarbazone To a solution of (2S-cis)-[5-(N-acetyl-(S)-aspartyl-β-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone (0.117 g, 0.178 mmol) in methylene chloride (1 mL) was added anisole (0.5 mL) followed by trifluoroacetic acid (1 mL). After stirring at room temperature under nitrogen for 2 hours, the reaction mixture was diluted with methylene chloride and evaporated, then chased twice with methylene chloride to give the title compound (0.099 g). TLC (methylene chloride-methanol-acetic acid, 13:6:1) R$_f$=0.2. Mass spectrum: m/z 560 (M+H).

EXAMPLE 7

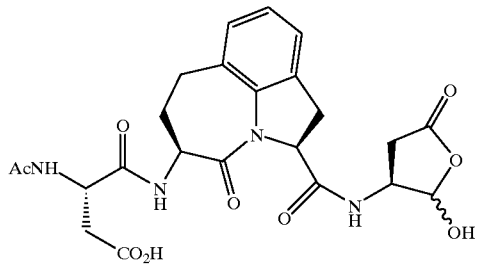

(2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic acid (2S-cis)-[5-(N-Acetyl-(S)-aspartyl)amino-1,2,3,4,5,6,7-hexahydro-4-oxoazepino[3,2,1-hi]indole-2-carbonyl)-amino]-4-oxo-butanoic acid semicarbazone (0.097 g, 0.177 mmol), was treated with a 3:1:1 solution of methanol-acetic acid-37% formaldehyde (2 mL) and the resulting mixture stirred under nitrogen for 1.5 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.050 g (56%) of the title compound as a white solid after lyophilization; m.p. 160–175° C. (dec). TLC (methylene chloride-methanol-acetic acid, 13:6:1) R$_f$=0.3. Mass spectrum: m/z 503 (M+H).

EXAMPLE 8

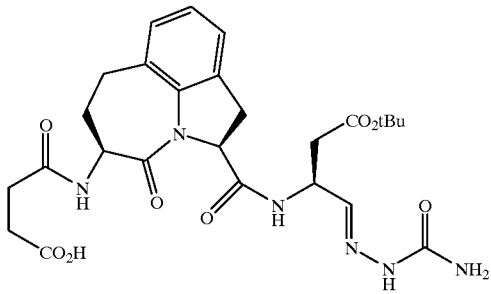

(2S-cis)-[5-Succinylamino-1,2,3,4,5,6,7-hexahydro-4-oxoazepino[3,2,1-hi]indole-2-carbonyl)-amino]-4-oxo-butanoic acid tert-butyl eater semicarbazone To a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.197 g, 0.435 mmol) in methylene chloride (6 mL) stirring at 0° C. under nitrogen was added succinic anhydride (0.057 g, 0.566 mmol), followed by pyridine (0.052 mL, 0.653 mmol). After stirring at room temperature under nitrogen for 3 hours, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 10% methanol-ethylene chloride then 80:19:1 methylene chloride-ethanol-acetic acid gave 0.216 g (88%) of the title compound as a white solid. TLC (methylene chloride-methanol-acetic acid, 8:1:1) $R_f$=0.5. Mass spectrum: m/z 557 (M−H).

EXAMPLE 9

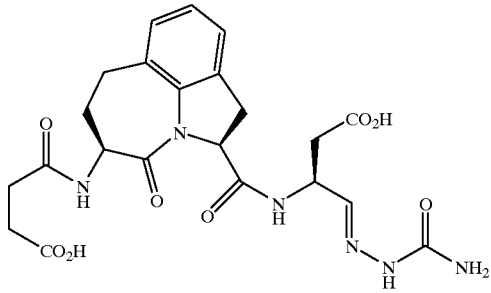

(2S-cis)-[5-Succinylamino-1,2,3,4,5,6,7-hexahydro-4-oxoazepino[3,2,1-hi]indole-2-carbonyl)-amino]-4-oxo-butanoic acid semicarbazone To a solution of (2S-cis)-[5-succinylamino-1,2,3,4,5,6,7-hexahydro-4-oxoazepino[3,2,1-hi]indole-2-carbonyl)-amino]-4-oxo-butanoic acid tert-butyl ester semicarbazone (0.191 g, 0.342 mmol) in methylene chloride (1 mL) was added anisole (0.5 mL) followed by trifluoroacetic acid (1 mL). After stirring at room temperature under nitrogen for 2 hours, the reaction mixture was diluted with methylene chloride and evaporated, then chased twice with methylene chloride to give the title compound (0.210 g). TLC (methylene chloride-methanol-acetic acid, 8:1:1) $R_f$=0.4. Mass spectrum: m/z 503 (M+H).

EXAMPLE 10

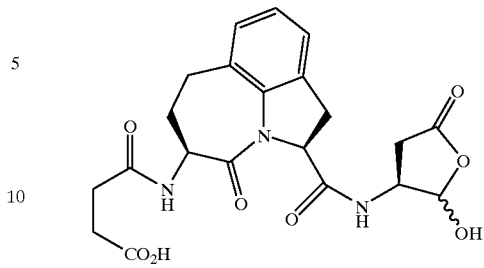

(2S-cis)-[5-Succinylamino-1,2,3,4,5,6,7-hexahydro-4-oxoazepino[3,2,1-hi]indole-2-carbonyl)-amino]-4-oxo-butanoic acid (2S-cis)-[5-Succinylamino-1,2,3,4,5,6,7-hexahydro-4-oxoazepino[3,2,1-hi]indole-2-carbonyl)-amino]-4-oxo-butanoic acid semicarbazone (0.208 g, ca. 0.342 mmol), was treated with a 3:1:1 solution of methanol-acetic acid-37% formaldehyde (3 mL), and the resulting mixture stirred under nitrogen for 1.5 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%-80% methanol-water gradient gave 0.064 g (42%) of the title compound as a white solid after lyophilization; m.p. 145–160° C. (dec). TLC (methylene chloride-methanol-acetic acid, 8:1:1) $R_f$=0.45. Mass spectrum: m/z 446 (M+H).

EXAMPLE 11

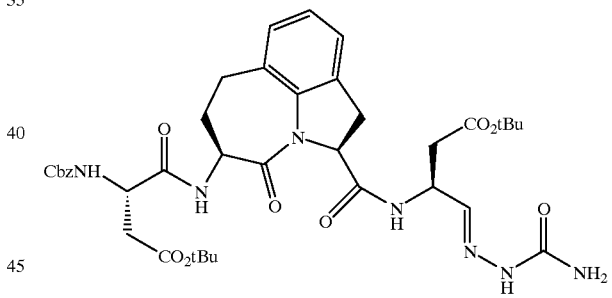

(2S-cis)-[5-(N-Benzyloxycarbonyl-(S)-aspartyl-β-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone To a solution of N-benzyloxycarbonyl-(S)-aspartyl-β-tert-butyl ester (0.169 g, 0.521 mmol) in methylene chloride (1.5 mL) stirring at 0° C. under nitrogen was added 1-hydroxybenzotriazole hydrate (0.087 g, 0.569 mmol) and 1-(3-dimethylaminopropyl)-3-ethylcarbodiimide hydrochloride (0.136 g, 0.711 mmol). After 15 minutes, a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.217 g, 0.474 mmol) in methylene chloride (2 mL) was added and the reaction was allowed to come to room temperature within 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 2% then 5% methanol-methylene chloride gave 0.244 g (67%) of the title compound as an off-white solid. TLC (methylene chloride-methanol, 9:1) $R_f$=0.55. $^1$H-NMR (300 MHz, CDCl$_3$) δ 9.13 (s, 1H), 7.85 (d, J=6 Hz, 1H), 7.56 (d, J=5.7 Hz, 1H) 7.23 (m, 5H), 7.08 (m, 1H), 7.00 (m, 2H), 5.13 (m, 3H) 4.77 (m, 1H), 4.62 (m, 1H), 4.43 (m, 1H), 3.60 (d, J=16 Hz, 1H), 3.22 (m, 2H), 2.98 (m, 1H), 2.83 (d, J=15.3 Hz, 1H), 2.65 & 2.36 (AB, dd, J=4.2, 7.7, 16.9 Hz, 2H), 2.42 (m, 1H), 2.10 (m, 1H), 1.35 (s, 9H), 1.24 (s, 9H).

EXAMPLE 12

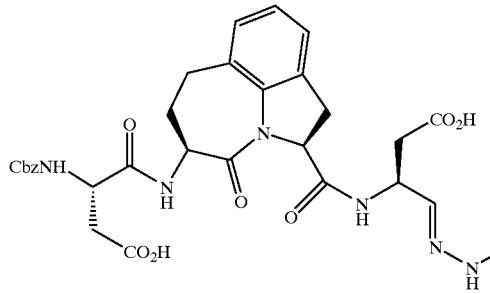

(2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid semicarbazone To a solution of (2S-cis)-[5-(N-Benzyloxycarbonyl-(S)-aspartyl-β-tert-butyl ester)amino-1,2,3,4,5,6,7-hexahydro-4-oxoazepino[3,2,1-hi]indole-2-carbonyl)-amino]-4-oxo-butanoic acid tert-butyl ester semicarbazone (0.217 g, 0.289 mmol) in methylene chloride (1 mL) was added anisole (0.5 mL) followed by trifluoroacetic acid (1 mL). After stirring at room temperature under nitrogen for 3 hours, the reaction mixture was diluted with methylene chloride and evaporated, then chased twice with methylene chloride to give the title compound (0.193 g). TLC (methylene chloride-methanol, 9:1) $R_f$=0.35. Mass spectrum: m/z 652 (M+H).

EXAMPLE 13

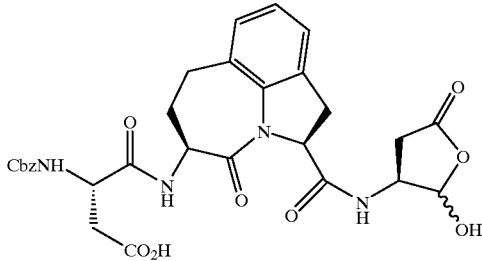

(2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid (2S-cis)-[5-(N-Benzyloxycarbonyl-(S)-aspartyl)amino-1,2,3,4,5,6,7-hexahydro-4-oxoazepino[3,2,1-hi]indole-2-carbonyl)-amino]-4-oxo-butanoic acid semicarbazone (0.191 g, 0.29 mmol), was treated with a 3:1:1 solution of methanol-acetic acid-37% formaldehyde (2 mL) and the resulting mixture stirred under nitrogen for 2 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.111 g. (64%) of the title compound as a white solid after lyophilization; m.p. 140–144° C. (dec.). TLC (methylene chloride-methanol, 9:1) $R_f$=0.4. Mass spectrum: m/z 593 (M-H).

EXAMPLE 14

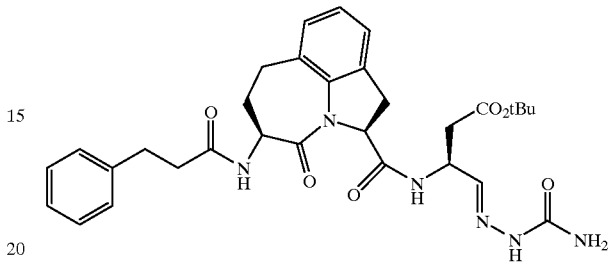

(2S-cis)-[5-Dihydrocinnamylamino-1,2,3,4,5,6,7-hexahydro-4-oxoazapino[3,2,1-hi]indole-2-carbonyl)-amino]-4-oxo-butanoic acid tert-butyl ester semicarbazone To a solution of dihydrocinnamic acid (0.169 g, 0.521 mmol) in methylene chloride (1.5 mL) stirring at 0° C. under nitrogen was added 1-hydroxybenzotriazole hydrate (0.088 g, 0.576 mmol) and 1-(3-dimethylaminopropyl)-3-ethylcarbodiimide hydrochloride (0.127 g, 0.665 mmol). After 15 minutes, a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.203 g, 0.443 mmol) in methylene chloride (2 mL), was added and the reaction was allowed to come to room temperature within 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 2 then 5% methanol-methylene chloride gave 0.208 g (79%) of the title compound as an off-white solid. TLC (methylene chloride-methanol, 9:1) $R_f$=0.7. $^1$H-NMR (300 MHz, CDCl$_3$) δ 8.82 (s, 1H), 7.72 (d, J=8.1 Hz, 1H), 7.19 (m, 5H), 7.06 (m, 1H), 7.01 (m, 2H), 6.76 (d, J=6.3, 1H), 5.23 (d, J=8.4 Hz, 1H0, 4.84 (m, 1H), 4.50 (m, 1H), 3.48 (m, 1H), 3.26 (m, 2H), 3.05 (m, 1H), 2.94 (m, 2H), 2.53 (m, 4H), 2.28 (m, 1H), 2.06 (m, 1H), 1.29 (s, 9H). Mass spectrum: m/z 591 (M+H).

EXAMPLE 15

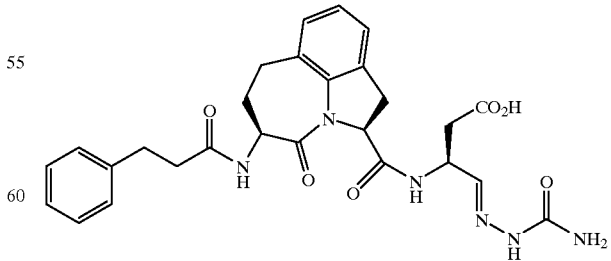

(2S-cis)-[5-Dihydrocinnamylamino-1,2,3,4,5,6,7-hexahydro-4-oxoazepino[3,2,1-hi]indole-2-carbonyl)-amino]-4-oxo-butanoic acid semicarbazone To a solution of (2S-cis)-[5-dihydrocinnamylamino-1,2,3,4,5,6,7-hexahydro-4-oxoazepino[3,2,1-hi]indole-2-carbonyl)-amino]-4-oxo-butanoic acid tert-butyl ester semicarbazone (0.189 g, 0.320 mmol) in methylene chloride (1 mL) was added anisole (0.5 mL) followed by trifluoroacetic acid (1 mL). After stirring at room temperature under nitrogen for 3 hours, the reaction mixture was diluted with methylene chloride and evaporated, then chased twice with methylene chloride to give the title compound (0.183 g). TLC (methylene chloride-methanol, 9:1) $R_f$=0.25. Mass spectrum: m/z 535 (M+H).

EXAMPLE 16

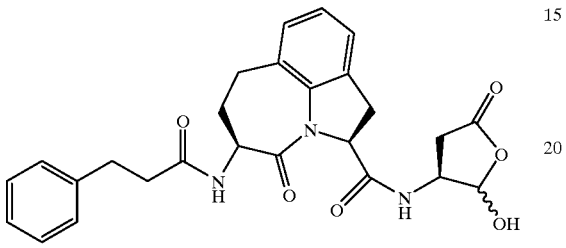

(2S-cis)-[5-Dihydrocinnamylamino-1,2,3,4,5,6,7-hexahydro-4-oxoazepino[3,2,1-hi]indole-2-carbonyl)-amino]-4-oxo-butanoic acid (2S-cis)-[5-Dihydrocinnamylamino-1,2,3,4,5,6,7-hexahydro-4-oxoazepino[3,2,1-hi]indole-2-carbonyl)-amino]-4-oxo-butanoic acid semicarbazone (0.181 g, ca. 0.320 mmol), was treated with a 3:1:1 solution of methanol-acetic acid-37% formaldehyde (2 mL) and the resulting mixture stirred under nitrogen for 4 hours. The reaction mixture was then diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.075 g (47%) of the title compound as a white solid after lyophilization; m.p. 78–81° C. TLC (methylene chloride-methanol, 9:1) $R_f$=0.45. $^1$H-NMR (300 MHz, DMSO d6) δ 8.58 (m, 1H), 8.30 (d, J=7.5 Hz, 1H), 7.24 (m, 5H), 7.08 (m, 2H), 6.99 (m, 1H), 5.04 (d, J=9.3 Hz, 1H), 4.39 (m, 1H), 4.19 (m, 1H), 3.46 (m, 1H), 3.05 (m, 2H), 2.93 (d, J=16.8 Hz, 2H), 2.83 (m, 2H), 2.00 (d, J=5.1 Hz, 2H). Mass spectrum: m/z 478 (M+H).

EXAMPLE 17

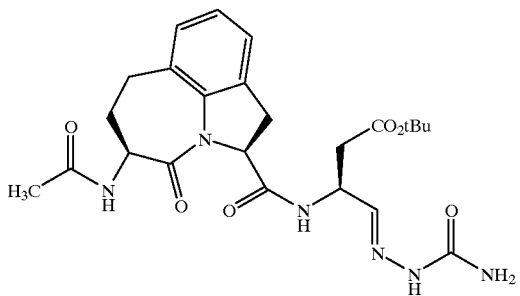

(2S-cis)-[5-Acetylamino-1,2,3,4,5,6,7-hexahydro-4-oxoazepino[3,2,1-hi]indole-2-carbonyl)-amino]-4-oxo-butanoic acid tert-butyl ester semicarbazone To a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.222 g, 0.490 mmol) in pyridine (3 mL) at room temperature under nitrogen was added acetic anhydride (0.07 mL, 0.735 mmol). After stirring overnight, the reaction mixture was diluted with methylene chloride and evaporated to give a foam. This was taken up in ethyl acetate and washed successively with 5% potassium bisulfate and saturated sodium chloride solutions; dried (sodium sulfate) and evaporated to dryness to give 0.130 g (53%) of the title compound as an off-white solid. TLC (methylene chloride-methanol, 9:1) $R_f$=0.55. $^1$H-NMR (300 MHz, CDCl$_3$) δ 8.75 (s, 1H), 7.75 (d, J=8.4 Hz, 1H), 7.08 (m, 1H), 7.01 (m, 2H), 6.87 (d, J=6.3 Hz, 1H), 5.25 (d, J=8.1 Hz, 1H), 4.84 (m, 1H), 4.52 (m, 1H), 3.50 (m, 1H), 3.28 (m, 2H), 3.02 (m, 1H), 2.55 & 2.46 (AB, dd, J=4.2, 7.1, 15.7 Hz, 2H), 2.36 (m, 1H), 2.18 (m, 1H), 2.02 (s, 3H), 1.31 (3, 9H).

EXAMPLE 18

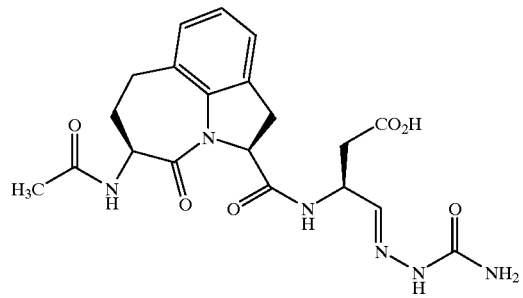

(2S-cis)-[5-Acetylamino-1,2,3,4,5,6,7-hexahydro-4-oxoazepino[3,2,1-hi]indole-2-carbonyl)-amino]-4-oxo-butanoic acid semicarbazone To a solution of (2S-cis)-[5-acetylamino-1,2,3,4,5,6,7-hexahydro-4-oxoazepino[3,2,1-hi]indole-2-carbonyl)-amino]-4-oxo-butanoic acid tert-butyl ester semicarbazone (0.112 g, 0.224 mmol) in methylene chloride (1 mL) was added anisole (0.5 mL) followed by trifluoroacetic acid (1 mL). After stirring at room temperature under nitrogen for 2.5 hours, the reaction mixture was diluted with methylene chloride and evaporated, then chased twice with methylene chloride to give the title compound (0.117 g). TLC (methylene chloride-methanol, 9:1) $R_f$=0.15. Mass spectrum: m/z 445 (M+H).

EXAMPLE 19

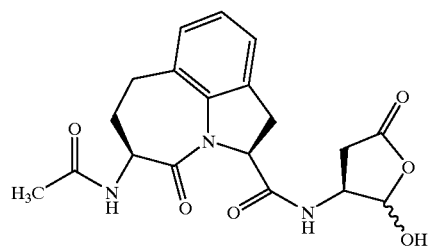

(2S-cis)-[5-Acetylamino-1,2,3,4,5,6,7-hexahydro-4-oxoazepino[3,2,1-hi]indole-2-carbonyl)-amino]-4-oxo-butanoic acid (2S-cis)-[5-Acetylamino-1,2,3,4,5,6,7-hexahydro-4-oxoazepino[3,2,1-hi]indole-2-carbonyl)-amino]-4-oxobutanoic acid semicarbazone (0.115 g, ca. 0.224 mmol) was treated with a 3:1:1 solution of methanol-acetic acid-37% formaldehyde (2 mL) and the resulting mixture stirred under nitrogen for 5 hours. The reaction mixture was diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.044 g (51%) of the title compound as a white solid after lyophilization; m.p. 210–215° C. (dec). TLC (methylene chloride-methanol-acetic acid, 44:5:1) $R_f$=0.45. Mass spectrum: m/z 388 (M+H).

EXAMPLE 20

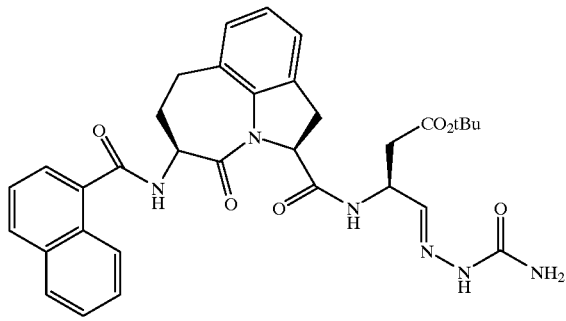

(2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid tert-butyl ester semicarbazone To a solution of 1-naphthoic acid (0.072 g, 0.417 mmol) in methylene chloride (1.5 mL) stirring at 0° C. under nitrogen was added 1-hydroxybenzotriazole hydrate (0.077 g, 0.501 mmol.) and 1-(3-dimethylaminopropyl)-3-ethylcarbodiimide hydrochloride (0.120 g, 0.626 mmol). After 15 minutes, a solution of (2S-cis)-[5-amino-1,2,3,4,5, 6,7-hexahydro-4-oxoazepino[3,2,1-hi]indole-2-carbonyl)-amino]-4-oxo-butanoic acid tert-butyl ester semicarbazone (0.189 g, 0.147 mmol) in methylene chloride (2 mL), was added and the reaction was allowed to come to room temperature within 1 hour. After stirring a total of 5 hours, the reaction mixture was diluted with ethyl acetate and washed successively with 5% potassium bisulfate and saturated sodium chloride solutions, dried (sodium sulfate) and evaporated to dryness. Purification of the crude product by flash chromatography on silica gel (S/P brand silica gel 60 Å, 230-400 mesh ASTM) eluting with 5% methanol-methylene chloride gave 0.168 g (66%) of the title compound as an off-white solid; m.p. 103–105° C. (dec.). TLC (methylene chloride-methanol, 9:1) $R_f$=0.6. Mass spectrum: m/z 613 (M+H). $^1$H-NMR (300 MHz, CDCl$_3$) δ 9.09 (bs, 1H), 8.38 (d, J=8.4 Hz, 1H), 7.82–7.93 (m, 3H), 7.70 (d, J=6.3 Hz, 1H), 7.45–7.58 (m, 3H), 7.37 (d, J=6.6 Hz, 1H), 7.06–7.15 (m, 4H), 5.30 (d, J=8.4 Hz, 1H), 4.80–4.85 (m, 2H), 3.57 (d, J=3.6 Hz, 1H), 3.30–3.45 (m, 2H), 3.16 (m, 1H), 2.59–2.65 (m, 2H), 2.27–2.49 (m, 2H), 1.29 (s, 9H).

EXAMPLE 21

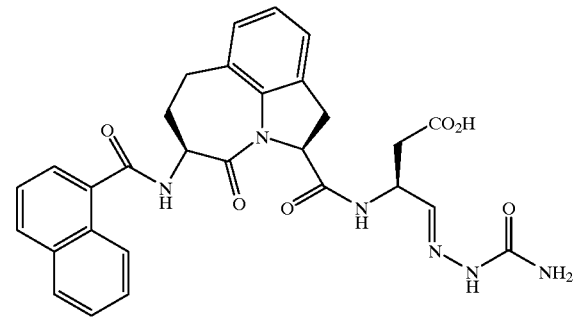

(2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid semicarbazone To a solution of (2-cis)-[5-(1-naphthoyl)amino-1,2,3,4,5, 6,7-hexahydro-4-oxoazepino[3,2,1-hi]indole-2-carbonyl)-amino]-4-oxo-butanoic acid tert-butyl ester semicarbazone (0.106 g, 0.173 mmol) in methylene chloride (1 mL) was added anisole (0.5 mL) followed by trifluoroacetic acid (1 mL). After stirring at room temperature under nitrogen for 3 hours, the reaction mixture was diluted with methylene chloride and evaporated, then chased twice with methylene chloride to give the title compound (0.110 g). TLC (methylene chloride-methanol, 9:1) $R_f$=0.3.

EXAMPLE 22

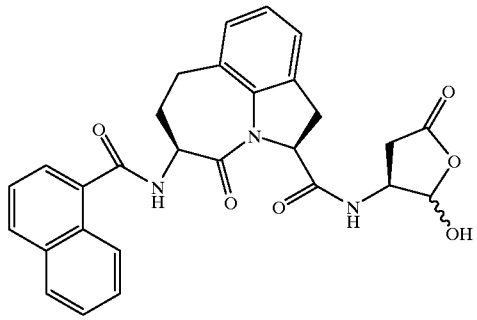

(2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid (2S-cis)-[5-(1-Naphthoyl)amino-1,2,3,4,5,6,7-hexahydro-4-oxoazepino[3,2,1-hi]indole-2-carbonyl)-amino]-4-oxo-butanoic acid semicarbazone (0.110 g, ca. 0.173 mmol) was treated with a 3:1:1 solution of methanol-acetic acid-37% formaldehyde (3 mL) and the resulting mixture stirred under nitrogen for 5 hours. The reaction mixture was then diluted with water, methanol removed by evaporation, then the remaining mixture lyophilized. Purification of the crude product by flash chromatography on silica gel (S/P brand silica gel 60 Å, 230-400 mesh ASTM) eluting with a 5%-20% methanol-methylene chloride gradient gave 0.076 g (86%) of the title compound as a white solid; m.p. 202–203° C. (dec). TLC(methylene chloride-methanol-acetic acid, 20:1:1) $R_f$=0.3. Mass spectrum: m/z 498 (M−H). $^1$H-NMR (300 MHz, CDCl$_3$) δ 9.38 (bs, 1H), 8.94 (m, 1H), 8.56 (m, 1H), 8.36 (m, 1H), 7.94–8.02 (m, 2H), 7.68 (d, J=6.9 Hz, 1H), 7.51–7.59 (m, 3H), 7.07–7.13

(m, 2H), 6.97 (m, 1H), 5.20 (d, J=10.5, 1 Hz), 4.67 (m, 1H), 4.15 (m, 1H), 3.49 (m, 1H), 2.95–3.23 (m, 2H), 2.53 (m, 1H), 2.22–2.34 (m, 2H).

EXAMPLE 23

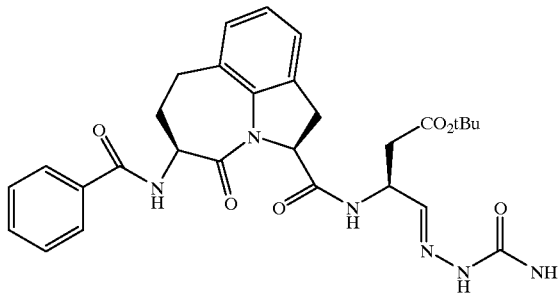

(2S-cis)-[5-Benzoylamino-1,2,3,4,5,6,7-hexahydro-4-oxoazepino[3,2,1-hi]indole-2-carbonyl)-amino]-4-oxo-butanoic acid tert-butyl ester semicarbazone To a solution of (2S-cis)-[5-amino-1,2,3,4,5,6,7-hexahydro-4-oxoazepino[3,2,1-hi]indole-2-carbonyl)-amino]-4-oxo-butanoic acid tert-butyl ester semicarbazone (0.121 g, 0.264 mmol) in methylene chloride (2.5 mL) stirring at 0° C. under nitrogen was added triethylamine (0.055 mL, 0.396 mmol), followed by benzoyl chloride (0.037 mL, 0.317 mmol). After stirring at room temperature under nitrogen for 1 hour, the reaction mixture was diluted with ethyl acetate and washed successively with 5% potassium bisulfate, saturated sodium bicarbonate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 10% hexane-ethyl acetate, 100% ethyl acetate, then 10% methanol-ethyl acetate gave 0.073 g (49%) of the title compound as a off-white solid. TLC (methylene chloride-methanol, 9:1) $R_f$=0.7. Mass spectrum: m/z 563 (M+H). $^1$H-NMR (300 MHz, CDCl$_3$) δ 8.61 (bs, 1H), 7.83–7.86 (m, 2H), 7.47–7.53 (m, 3H), 7.06–7.12 (m, 3H), 5.30 (dd, J=2.2, 7.8 Hz, 1H), 4.89 (m, 1H), 4.72 (m, 1H), 3.60 (d, J=16.5 Hz, 1H), 3.36 (m, H), 3.19 (m, 1H), 2.69 (dd, J=4.4, 11.7 Hz, 1H), 2.52 (m, 1H), 2.29 (m, 1H), 1.34 (s, 9H).

EXAMPLE 24

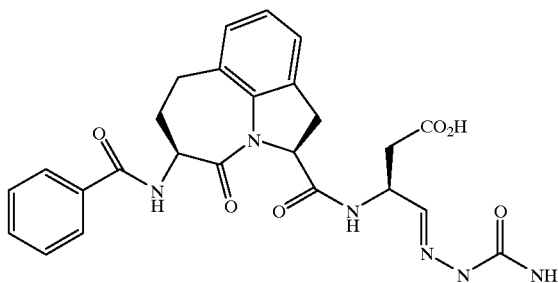

(2S-cis)-[5-Benzoylamino-1,2,3,4,5,6,7-hexahydro-4-oxoazepino[3,2,1-hi]indole-2-carbonyl)-amino]-4-oxo-butanoic acid semicarbazone To a solution of (2S-cis)-[5-benzoylamino-1,2,3,4,5,6,7-hexahydro-4-oxoazepino[3,2,1-hi]indole-2-carbonyl)-amino]-4-oxo-butanoic acid tert-butyl ester semicarbazone (0.064 g, 0.114 mmol) in methylene chloride (1 mL) was added anisole (0.5 mL) followed by trifluoroacetic acid (1 mL). After stirring at room temperature under nitrogen for 2.5 hours, the reaction mixture was diluted with ethyl acetate and evaporated to give the title compound (0.070 g). TLC (methylene chloride-methanol, 4:1) $R_f$=0.4. Mass spectrum: m/z 507 (M+H).

EXAMPLE 25

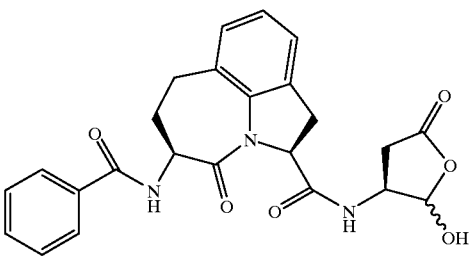

(2S-cis)-[5-Benzoylamino-1,2,3,4,5,6,7-hexahydra-4-oxoazepino[3,2,1-hi]indole-2-carbonyl)-amino]-4-oxo-butanoic acid (2S-cis)-[5-Benzoylamino-1,2,3,4,5,6,7-hexahydro-4-oxoazepino[3,2,1-hi]indole-2-carbonyl)-amino]-4-oxo-butanoic acid semicarbazone (0.070 g, ca. 0.114 mmol) was treated with a 3:1:1 solution of methanol-acetic acid-37% formaldehyde (3 mL), and the resulting mixture stirred under nitrogen for 3.5 hours. The reaction mixture was then diluted with water, methanol removed by evaporation, then the remaining mixture lyophilized. Purification of the crude product by flash chromatography on silica gel (S/P brand silica gel 60 Å, 230-400 mesh ASTM) eluting with 10 and 20% methanol-methylene chloride gave 0.042 g (82%) of the title compound as a white solid; m.p. 204–205° C. (dec). TLC (methylene chloride-methanol, 4:1) $R_f$=0.4. Mass spectrum: m/z 448 (M−H). $^1$H-NMR (300 MHz, DMSO-d$_6$) δ 8.84 (m, 1H), 8.53 (m, 1H), 7.91–7.95 (m, 2H), 7.46–7.58 (m, 3H), 7.11 (m, 2H), 6.99 (t, J=7.3 Hz, 1H), 5.14 (d, 10.2 Hz, 1H), 4.62 (m, 1H), 4.23 (m, 1H), 3.48 (m, 1H), 3.12–3.18 (m, 2H), 2.99 (m, 1H), 2.58 (m, 1H), 2.12–2.46 (m, 3H).

EXAMPLE 26

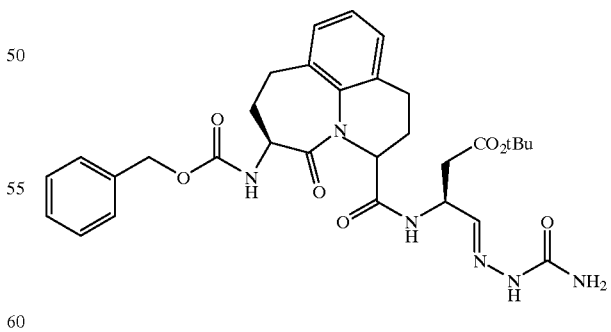

(3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid tert-butyl ester semicarbazone To a solution of (3R,S-cis)-6-benzyloxycarbonylamino-5-oxo-2,3,4,5,6,7,8-hexahydro-1H-azepino[3,2,1-hi] quinoline-3-carboxylic acid (0.604 g, 1.5 mmol) in methylene chloride (12 mL) stirring at 0° C. under nitrogen was added 1-hydroxybenzotriazole hydrate (0.282 g, 1.8 mmol) and 1-(3-dimethylaminopropyl)-3-ethylcarbodiimide hydrochloride (0.442 g, 3 mmol). After 15 minutes, L-aspartic acid semicarbazone β-tert-butyl ester, p-toluenesulfonate salt (0.60 g, 1.5 mmol) and N-methylmorpholine (0.25 mL, 3 mmol) were added and the mixture allowed to come to room temperature within 1 hour. After stirring an additional hour, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 10% methanol-methylene chloride gave 0.523 g (56%) of the title compound as a white foam. TLC (methylene chloride-methanol, 9:1) $R_f$=0.65. $^1$H-NMR (300 MHz, CDCl$_3$) δ 9.89 (m, 1H), 7.72 (m, 1H), 7.92 (d, J=9 Hz, 1H), 7.65 (d, J=8.1 Hz, 1H), 7.32–7.28 (m, 5H), 7.12 (s, 1H), 7.07 (d, J=5.7 Hz, 2H), 6.03 (d, J=7.5 Hz, 1H), 5.84 (d, J=8.1 Hz, 1H), 5.03 (s, 2H), 5.01 (m, 1H) 4.80 (m, 1H), 4.31 (m, 1H), 2.98 (m, 1H), 2.75–2.41 (m, 7H), 2.12 (m, 1H), 1.77 (m, 1H), 1.39 (s, 9H).

EXAMPLE 27

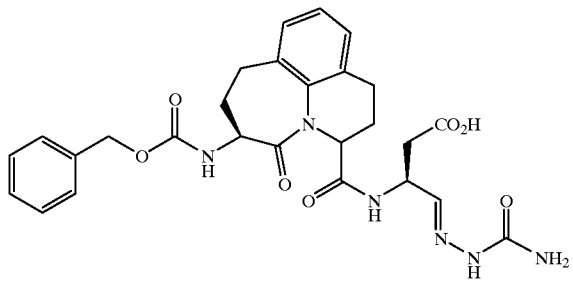

(3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid semicarbazone To a solution of (3R,S-cis)-6-Benzyloxycarbonylamino-5-oxo-2,3,4,5,6,7,8-hexahydro-1H-azepino[3,2,1-hi] quinoline-3-carbonyl)-amino]-4-oxo-butanoic acid tert-butyl ester semicarbazone (0.200 g, 0.33 mmol) in methylene chloride (1 mL) was added anisole (0.5 mL, 4.62 mmol) followed by trifluoroacetic acid (1 mL). After stirring at room temperature under nitrogen for 1.5 hours the reaction mixture was diluted with methylene chloride and evaporated, then azeotroped twice with methylene chloride to give the title compound (0.248 g). TLC (methylene chloride-methanol-acetic acid, 8:1:1) $R_f$=0.2. Mass spectrum: m/z 549 [M–H]$^-$.

EXAMPLE 28

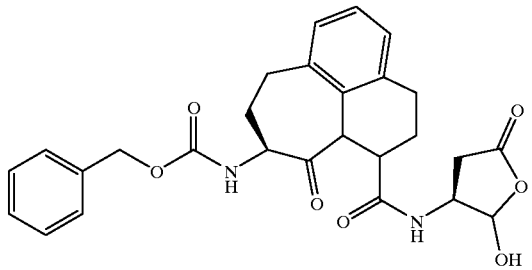

(3R,S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid (3R, S-cis)-6-Benzyloxycarbonylamino-5-oxo-2,3,4,5,6,7,8-hexahydro-1H-azepino[3,2,1-hi]quinoline-3-carbonyl)-amino]-4-oxo-butanoic acid semicarbazone (0.245 g, ca 0.33 mmol), was treated with a 3:1:1 solution of methanol-acetic acid-37% formaldehyde (3 mL) and the resulting mixture stirred under nitrogen for 1.5 hours. The reaction mixture was diluted with water, methanol removed by evaporation, then the remaining mixture lyophilized. Purification of the crude product by flash chromatography on reverse phase gel (MCI gel, CHP-20P, 75–150 micron) eluting with a 10%–80% methanol-water gradient gave 0.090 g (60%) of the title compound as a white solid after lyophilization; m.p. 120–123° C. (dec). TLC (methylene chloride-methanol-acetic acid, 32:1:1) $R_f$=0.45. $^1$H-NMR (300 MHz, DMSO d6) δ 8.67 (m, 1H), 7.79 (m, 1H), 7.57 (m, 1H), 7.37–7.27 (m, 5H), 7.17–7.08 (m, 3H), 5.44 (m, 1H), 4.95 (s, 2H), 4.70 (m, 1H), 4.07 (m, 1H), 3.92 (m, 1H), 3.16 (m, 1H), 2.98 (m, 1H), 2.75–2.41 (m, 7H), 2.25 (m, 1H), 2.11 (m, 1H), 1.29 (m, 1H). Mass spectrum: m/z 492 [M–H]$^-$.

EXAMPLE 29

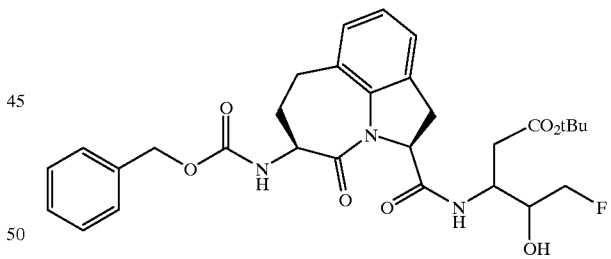

3{(2S-cis)-[5-Benzyloxycarbonylamino-1,2,3,4,5,6,7-hexahydro-4-oxoazopino[3,2,1-hi]indole-2-carbonyl)-amino]}-5-fluoro-4-hydroxy-pentanoic acid tert-butyl ester To a solution of (2S-cis)-5-benzyloxycarbonylamino-1,2,3,4,5,6,7-hexahydro-4-oxoazepino[3,2,1-hi]indole-2-carboxylic acid (0.373 g, 0.98 mmol) in methylene chloride (3 mL) stirring at 0° C. under nitrogen was added 1-hydroxybenzotriazole hydrate (0.151 g, 0.98 mmol) and 1-(3-dimethylaminopropyl)-3-ethylcarbodiimide hydrochloride (0.283 g, 1.47 mmol). After 15 minutes, 3-amino-4-hydroxy-5-fluoropentanoic acid, tert-butyl ester (0.204 g, 0.98 mmol, prepared as described in Tetrahedron Letters 35, pp. 9693–9696 (1994)) was added and the mixture allowed

EXAMPLE 31

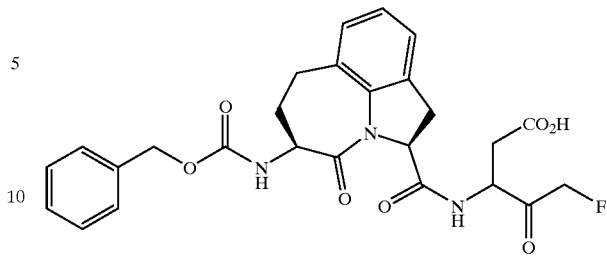

3{(2S-cis)-[5-Benzyloxycarbonylamino-1,2,3,4,5,6,7-hexahydro-4-oxoazepino[3,2,1-hi]indole-2-carbonyl)-amino]}-5-fluoro-4-oxo-pentanoic acid To a solution of 3{(2S-cis)-[5-benzyloxycarbonylamino-1,2,3,4,5,6,7-hexahydro-4-oxoazepino[3,2,1-hi]indole-2-carbonyl)-amino]}-5-fluoro- 4-oxo-pentanoic acid tert-butyl ester (0.063 g, 0.111 mmol) in methylene chloride (1.0 mL) was added anisole (0.5 mL), followed by trifluoroacetic acid (1.0 mL). After stirring at room temperature under nitrogen for 2 hours the reaction mixture was diluted with methylene chloride and evaporated, then chased twice with methylene chloride. The crude residue was triturated with ethyl ether to give 0.030 g of the titled product as a white solid; m.p. 106–107° C. (dec). TLC (methylene chloride-methanol-acetic acid, 32:1:1) $R_f$=0.3. $^1$H-NMR (300 MHz, CDCl$_3$) δ 7.61 (m, 1H), 7.32 (s, 5H), 7.1 (d, J=4 Hz, 1H), 7.03 (d, J=4 Hz, 2H), 6.17 (m, 1H), 5.22 (m, 1H), 5.10 (s, 2H), 4.75–4.70 (m, 2H), 4.32 (m, 1H), 3.5 (m, 1H), 3.31–3.15 (m, 2H), 3.03 (m, 1H), 2.93 (m, 1H), 2.69 (m, 1H), 2.36 (m, 1H), 2.12 (m, 1H). Mass spectrum: m/z 512 (M+H).

EXAMPLE 30

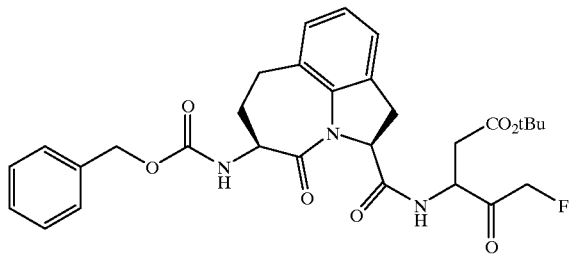

3{(2S-cis)-[5-Benzyloxycarbonylamino-1,2,3,4,5,6,7-hexahydro-4-oxoazepino[3,2,1-hi]indole-2-carbonyl)-amino]}-5-fluoro-4-oxo-pentanoic acid tert-butyl ester To a solution of 3{(2S-cis)-[5-benzyloxycarbonylamino-1,2,3,4,5,6,7-hexahydro-4-oxoazepino[3,2,1-hi]indole-2-carbonyl)-amino]}-5-fluoro-4-hydroxy-pentanoic acid tert-butyl ester (0.114 g, 0.20 mmol) in methyl sulfoxide (1.3 mL) was added Dess-Martin periodinane (0.228 g). After stirring at room temperature under nitrogen for 2 hours an additional portion of Dess-Martin periodinane (0.135 g) was added followed 2.5 hours later by a third portion (0.10 g). The reaction mixture was diluted with ethyl acetate and washed twice with water and saturated sodium chloride solution; dried (sodium sulfate) and evaporated to dryness. Purification of the crude product by flash chromatography on silica gel (S/P brand silica gel 60 Å, 230-400 mesh ASTM) eluting 1/1 ethyl acetate-hexanes gave 0.076 g (67%) of the title compound as a white foam. TLC (ethyl acetate-hexanes, 1:1) $R_f$=0.6. $^1$H-NMR (300 MHz, CDCl$_3$) δ 7.58 (d, J=8.4 Hz, 1H), 7.34–7.30 (m, 5H), 7.07–6.99 (m, 3H), 6.06 (m, 1H), 5.23 (d, J=12.3 Hz, 1H), 5.12 (s, 2H), 4.53 (d, J=13.2 Hz, 1H), 4.77 (d, J=9.9 Hz, 2H), 4.32 (m, 1H), 3.44 (dd, J=5, 8.4 Hz, 1H), 3.32–3.21 (m, 2H), 3.06 (m, 1H), 2.9 (m, 1H), 2.62 (m, 1H), 2.41 (m, 1H), 2.17 (m, 1H), 1.39 (s, 4H), 1.29 (s, 5H).

to come to room temperature within 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with 2% methanol-methylene chloride gave 0.383 g (68%) of the title compound as a white foam. TLC (methylene chloride-methanol, 9:1) $R_f$=0.6. $^1$H-NMR (300 MHz, CDCl$_3$) δ 7.45–7.31 (m, 5H), 7.08–7.01 (m, 3H), 6.10 (m, 1H), 5.26 (m, 1H), 5.12 (s, 2H), 4.52 (m, 1H), 4.38–4.30 (m, 2H), 4.21–4.19 (m, 2H), 4.03–3.95 (m, 2H), 3.43–3.20 (m, 4H), 3.13 (m, 2H), 2.62–2.50 (m, 2H), 2.42 (m, 1H), 1.42 (s, 4H), 1.32 (s, 5H). Mass spectrum: m/z 570 (M+H).

EXAMPLE 32

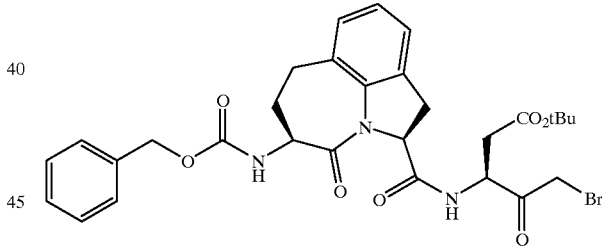

3-[(2S-cis)-[5-Benzyloxycarbonylamino-1,2,3,4,5,6,7-hexahydro-4-oxoazepino[3,2,1-hi]indole-2-carbonyl]amino]-5-bromo-4-oxo-pentanoic acid, tart-butyl ester To a solution of (2S-cis)-5-benzyloxycarbonylamino-1,2,3,4,5,6,7-hexahydro-4-oxoazepino[3,2,1-hi]indole-2-carboxylic acid (0.302 g, 0.797 mmol) in methylene chloride (5.5 mL) stirring at 0° C. under nitrogen was added 1-hydroxybenzotriazole hydrate (0.146 g, 0.96 mmol) and 1-(3-dimethylaminopropyl)-3-ethylcarbodiimide hydrochloride (0.230 g, 1.2 mmol). After 15 minutes, aspartic acid, α-methyl, β-tert-butyl diester hydrochloride (0.191 g, 0.797 mmol) was added followed by N-methylmorpholine (0.13 mL, 1.2 mmol) and the mixture allowed to come to room temperature within 1 hour. After stirring overnight, the reaction mixture was diluted with ethyl acetate and washed successively with 5% potassium bisulfate and saturated sodium chloride solutions; dried (sodium sulfate) and evaporated to dryness. Purification of the crude product by flash chromatography on silica gel (S/P brand silica gel 60 Å, 230-400 mesh ASTM) eluting with ethyl acetate-hexane (1:1) gave 0.350 g (78%) of N-[(2S-cis)-[5-benzyloxycarbonylamino-1,2,3,4,5,6,7-hexahydro-4-oxoazepino[3,2,1-hi]indole-2-carbonyl]]aspartic acid, α-methyl, β-tert-butyl diester as a white solid. TLC (methylene chloride-methanol, 9:1 $R_f$=0.8. m.p. 147–148° C. (dec.). $^1$H-NMR (300 MHz, CDCl$_3$): δ 7.48 (d, J=7.5 Hz, 1H), 7.34–7.29 (m, 5H), 7.07 (m, 1H), 7.03–6.96 (m, 2H), 6.15 (d, J=5.7 Hz, 1H), 5.28 (d, J=7.8 Hz 1H), 5.11 (s, 2H), 4.72 (m, 1H), 4.32 (m, 1H), 3.74 (s, 3H), 3.49 (d, J=16.5 Hz, 1H), 3.31–3.20 (m, 2H), 3.05 (m, 1H), 2.72 (ABX, dd, J=4.65, 15, 64.5 Hz, 2H), 2.43 (m, 1H), 2.15 (m, 1H), 1.30 (s, 9H).

To a solution of the above product (0.330 g, 0.585 mmol) in 1,4-dioxane (4.5 mL) and water (1.5 mL) was added 1M aqueous lithium hydroxide (0.7 mL, 0.702 mmol) and the resulting mixture was stirred at room temperature under nitrogen for 30 minutes. The reaction mixture was acidified to pH 3 with a 0.1N HCl solution, then partitioned between ethyl acetate and saturated sodium chloride solution. The aqueous layer was back extracted two times with ethyl acetate, and the combined organic layers were dried (sodium sulfate) and evaporated to yield 0.275 g (85%) of N-[(2S-cis)-[5-benzyloxycarbonylamino-1,2,3,4,5,6,7-hexahydro-4-oxoazepino[3,2,1-hi]indole-2-carbonyl]]aspartic acid, β-tert-butyl ester as a white foam. TLC (methylene chloride-methanol, 9:1): $R_f$=0.25. $^1$H-NMR (300 MHz, CDCl$_3$): δ 7.57 (d, J=7.8 Hz, 1H), d7.35–7.29 (m, 5H), 7.08 (m, 1H), 7.03–6.98 (m, 2H), 6.24 (d, J=6 Hz, 1H), 5.28 (d, J=5.1 Hz 1H), 5.11 (s, 2H), 4.73 (m, 1H), 4.35 (m, 1H), 3.48 (d, J=16.8 Hz, 1H), 3.36–3.20 (m, 2H), 3.07 (m, 1H), 2.76 (ABX, dd, J=4.8, 18, 66 Hz, 2H), 2.40 (m, 1H), 2.19 (m, 1H), 1.33 (s, 9H).

To a solution of the above product (0.262 g, 0.475 mmol) in tetrahydrofuran (3.0 mL) stirring at −10° C. under nitrogen was added N-methylmorpholine (0.114 mL, 1.05 mmol) followed by dropwise addition of isobutyl chloroformate (0.107 mL, 0.81 mmol). After 40 minutes the reaction mixture was filtered, the salts washed with dry THF, and the filtrate cooled to 0° C. This was treated with a freshly prepared ethereal solution of diazomethane (excess). After stirring the mixture at 0° C. for 30 minutes, a mixture of hydrobromic acid (48% wt. aq. solution)/acetic acid (1.3 mL, 1/1) was added dropwise. After stirring for another 10 minutes, the reaction mixture was diluted with ethyl acetate, then washed successively with saturated sodium bicarbonate and saturated sodium chloride solutions; dried (sodium sulfate) and evaporated to dryness. Purification of the crude product by flash chromatography on silica gel (S/P brand silica gel 60 Å, 230-400 mesh ASTM) eluting with ethyl acetate-hexane (1:1) gave 0.200 g (67%) of the title compound as a white foam. TLC (ethyl acetate-hexane, 1:1): $R_f$=0.7. $^1$H-NMR (300 MHz, CDCl$_3$): δ 7.71 (d, J=9 Hz, 1H), d7.35–7.30 (m, 5H), 7.09 (m, 1H), 7.04–7.02 (m, 2H), 6.1 (d, J=5.4 Hz, 1H), 5.28 (d, J=7.2 Hz 1H), 5.12 (s, 2H), 4.89 (dd, J=4.5, 15 Hz 1H), 4.35 (m, 1H), 4.16 (s, 2H), 3.50–3.21 (m, 3H), 3.06 (m, 1H), 2.76 (ABX, dd, J=4.65, 18, 103 Hz, 2H), 2.37 (m, 1H), 2.15 (m, 1H), 1.27 (s, 9H). Mass spectrum: m/z 626/628 (M−H).

EXAMPLE 33

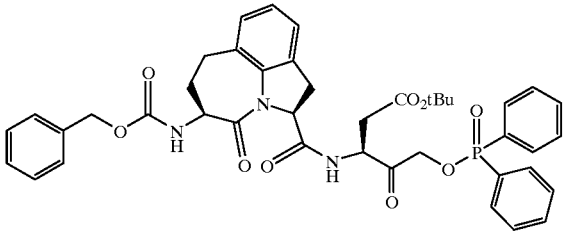

3-[(2S-cis)-[5-Benzyloxycarbonylamino-1,2,3,4,5,6,7-hexahydro-4-oxoazepino[3,2,1-hi]indole-2-carbonyl]amino]-5-(diphenylphosphinyl)oxy-4-oxo-pentanoic acid, tert-butyl ester To a solution of 3-[(2S-cis)-[5-benzyloxycarbonylamino-1,2,3,4,5,6,7-hexahydro-4-oxoazepino[3,2,1-hi]indole-2-carbonyl]amino]-5-bromo-4-oxo-pentanoic acid, tert-butyl ester (0.069 g, 0.110 mmol) in N,N-dimethylformamide (1.0 mL) was added potassium fluoride (0.029 g, 0.495 mmol), followed diphenylphosphinyl acid (0.029 g, 0.139 mmol). After stirring at room temperature under nitrogen for 48 hours, the reaction mixture was diluted with ethyl acetate, then washed successively with a dilute sodium bicarbonate solution then water; dried (sodium sulfate) and evaporated to dryness. Purification of the crude product by flash chromatography on silica gel (S/P brand silica gel 60 Å, 230-400 mesh ASTM) eluting with ethyl acetate-hexane (1:1) gave 0.048 g (59%) of the title compound as a clear oil. TLC (ethyl acetate-hexane, 2:1): $R_f$=0.3. $^1$H-NMR (300 MHz, CDCl$_3$): δ 7.89–7.80 (m, 4H), 7.52–7.30 (m, 11H), 7.06 (m, 1H), 7.01–6.96 (m, 2H), 6.45 (m, 1H), 5.21 (m, 1H), 5.13 (s, 2H), 4.96 (dd, J=8.3, 18 Hz, 1H), 4.78–4.70 (m, 2H), 4.35 (m, 1H), 3.35–3.23 (m, 3H), 3.05 (m, 1H), 2.76 (ABX, dd, J=4.65, 18, 103 Hz, 2H), 2.43 (m, 1H), 2.18 (m, 1H), 1.33 (s, 9H).

EXAMPLE 34

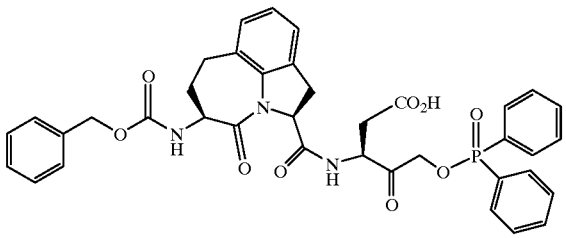

3-[(2S-cis)-[5-Benzyloxycarbonylamino-1,2,3,4,5,6,7-hexahydro-4-oxoazapino[3,2,1-hi]indole-2-carbonyl]amino]5-(diphenylphosphinyl) oxy-4-oxo-pentanoic acid To a solution of 3-[(2S-cis)-[5-benzyloxycarbonylamino-1,2,3,4,5,6,7-hexahydro-4-oxoazepino[3,2,1-hi]indole-2-carbonyl]amino]-5-(diphenylphosphinyl)oxy-4-oxo-pentanoic acid, tert-butyl ester (0.040 g, 0.054 mmol) in methylene chloride (1.0 mL) was added anisole (0.5 mL), followed by trifluoroacetic acid (1.0 mL). After stirring at room temperature under nitrogen for 30 minutes the reaction mixture was diluted with methylene chloride and evaporated, then azeotroped twice with methylene chloride. The crude residue was triturated with ethyl ether to give 0.030 g of the titled product as a white solid; m.p. 109–111° C. (dec). TLC (methylene chloride-methanol, 9:1): $R_f$=0.4.

$^1$H-NMR (300 MHz, CDCl$_3$): δ 7.87–7.66 (m, 4H), 7.60–7.28 (m, 11H), 7.05–6.95 (m, 3H), 6.84 (m, 1H), 5.12 (s, 2H), 5.05 (m, 1H), 4.58 (m, 1H), 4.42–4.15 (m, 4H), 3.35–3.10 (m, 4H), 3.05 (m, 1H), 2.76 (m, 1H), 2.56 (m, 1H), 2.37 (m, 1H), 2.13 (m, 1H), 1.93 (bs, 1H). Mass spectrum: m/z 710 (M+H).

We claim:

1. A method of preventing or mitigating ischemic injury to a patient suffering from a disease having the potential to cause such an injury comprising administering, to a patient in need of such treatment, an effective amount of a pharmaceutical composition comprising a compound of the formula:

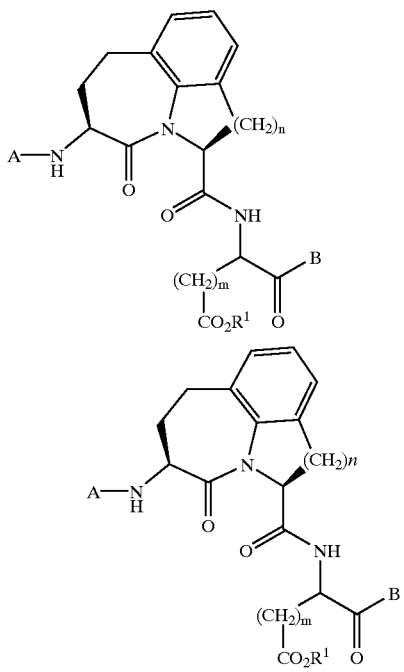

wherein:

n is 1 or 2;
m is 1 or 2;
A is R$^2$CO—, R$^3$—O—CO—, or R$^4$SO$_2$—;
a group of the formula:

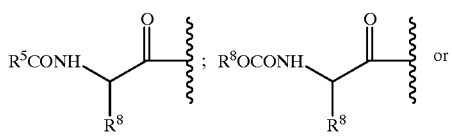

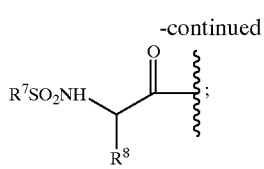

further wherein:

R$^1$ is a hydrogen atom, alkyl or phenylalkyl;

R$^2$ is alkyl, cycloalkyl, (cycloalkyl)alkyl, phenyl, phenylalkyl, substituted phenyl, (substituted phenyl)alkyl, heteroaryl, or (heteroaryl)alkyl;

R$^3$ is alkyl, cycloalkyl, (cycloalkyl)alkyl, phenylalkyl or (substituted phenyl)alkyl;

R$^4$ is alkyl, cycloalkyl, (cycloalkyl)alkyl, phenyl, phenylalkyl, substituted phenyl, (substituted phenyl)alkyl, heteroaryl, or (heteroaryl)alkyl;

R$^5$ is alkyl, cycloalkyl, (cycloalkyl)alkyl, phenyl, phenylalkyl, heterozryl, or (heteroaryl)alkyl;

R$^6$ is alkyl, cycloalkyl, (cycloalkyl)alkyl, phenylalkyl, or (substituted phenyl)alkyl;

R$^7$ is alkyl, cycloalkyl, (cycloalkyl)alkyl, phenyl, phenylalkyl, substituted phenyl, (substituted phenyl)alkyl, heteroaryl, or (heteroaryl)alkyl;

R$^8$ is an amino acid side chain chosen from the group consisting of natural and unnatural amino acids;

B is a hydrogen atom, a deuterium atom, alkyl, cycloalkyl, (cycloalkyl)alkyl, phenyl, phenylalkyl, substituted phenyl, (substituted phenyl)alkyl, heteroaryl, (heteroaryl)alkyl, or halomethyl;

a group of the formula:

wherein R$^9$ is phenyl, substituted phenyl, phenylalkyl, (substituted phenyl)alkyl, heteroaryl, and (heteroaryl)alkyl; and X is an oxygen or a sulfur atom;

a group of the formula:

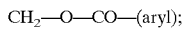

or a group of the formula:

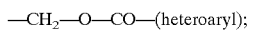

a group of the formula:

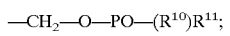

wherein R$^{10}$ and R$^{11}$ are independently selected from a group consisting of alkyl, cycloalkyl, phenyl, substituted phenyl, phenylalkyl, and (substituted phenyl)alkyl;

and a pharmaceutically-acceptable salt thereof.

* * * * *

UNITED STATES PATENT AND TRADEMARK OFFICE
CERTIFICATE OF CORRECTION

PATENT NO. : 6,444,663 B2
DATED : September 3, 2002
INVENTOR(S) : Donald S. Karanewsky et al.

It is certified that error appears in the above-identified patent and that said Letters Patent is hereby corrected as shown below:

Title page,
Item [56], References Cited, OTHER PUBLICATIONS, "Robl et al., "Synthesis of Benzo-Fused, 7,5-and 7,6-Fused Azepinones as Conformationally Restricted Dipeptide Mometics," *Tetrahedron Letters 36*:1593-1596 (1995)." should read -- Robl et al., "Synthesis of Benzo-Fused, 7,5-and 7,6-Fused Azepinones as Conformationally Restricted Dipeptide Mimetics," *Tetrahedron Letters 36*:1593-1596 (1995). --.

Column 45,
Claim 1, lines 15-40, the following formula:
"

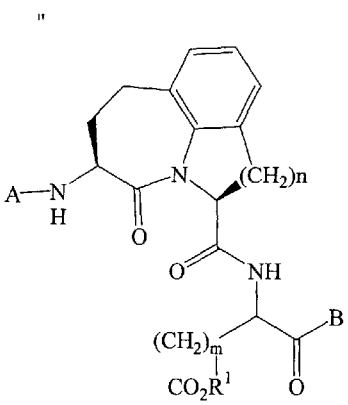

"

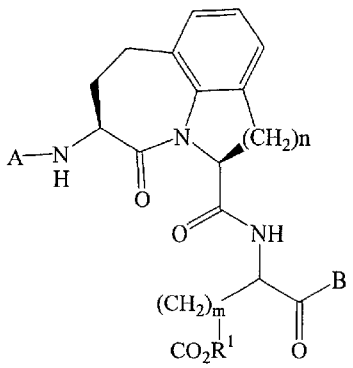

UNITED STATES PATENT AND TRADEMARK OFFICE
CERTIFICATE OF CORRECTION

PATENT NO. : 6,444,663 B2
DATED : September 3, 2002
INVENTOR(S) : Donald S. Karanewsky et al.

It is certified that error appears in the above-identified patent and that said Letters Patent is hereby corrected as shown below:

should read
--

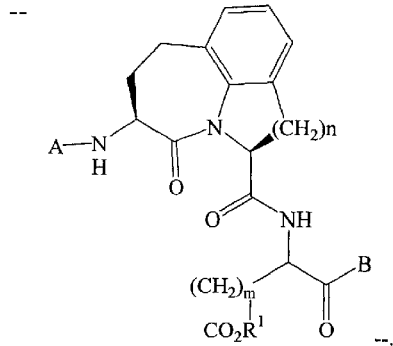

--.

Signed and Sealed this

Twenty-ninth Day of April, 2003

JAMES E. ROGAN
*Director of the United States Patent and Trademark Office*